US009803028B2

(12) United States Patent
Pettersson et al.

(10) Patent No.: US 9,803,028 B2
(45) Date of Patent: Oct. 31, 2017

(54) ANTIBODIES AGAINST PHOSPHORYLCHOLINE

(75) Inventors: Knut Pettersson, Göteborg (SE); Ola Camber, Bromma (SE); Dan Sexton, Melrose, MA (US); Andrew E. Nixon, Hanover, MA (US)

(73) Assignees: ATHERA BIOTECHNOLOGIES AB, Stockholm (SE); DYAX CORP., Burlington, MA (US)

( * ) Notice: Subject to any disclaimer, the term of this patent is extended or adjusted under 35 U.S.C. 154(b) by 728 days.

(21) Appl. No.: 14/237,035

(22) PCT Filed: Aug. 8, 2012

(86) PCT No.: PCT/EP2012/065505
§ 371 (c)(1),
(2), (4) Date: Feb. 4, 2014

(87) PCT Pub. No.: WO2013/020995
PCT Pub. Date: Feb. 14, 2013

(65) Prior Publication Data
US 2014/0178410 A1 Jun. 26, 2014

Related U.S. Application Data

(60) Provisional application No. 61/521,593, filed on Aug. 9, 2011.

(51) Int. Cl.
*C07K 16/44* (2006.01)
*A61K 39/00* (2006.01)

(52) U.S. Cl.
CPC ........ *C07K 16/44* (2013.01); *A61K 2039/505* (2013.01); *C07K 2317/21* (2013.01); *C07K 2317/55* (2013.01); *C07K 2317/565* (2013.01); *C07K 2317/567* (2013.01); *C07K 2317/70* (2013.01); *C07K 2317/92* (2013.01)

(58) Field of Classification Search
None
See application file for complete search history.

(56) References Cited

U.S. PATENT DOCUMENTS

| 4,203,893 | A | 5/1980 | Pery et al. |
| 5,455,032 | A | 10/1995 | Kenny et al. |
| 5,475,100 | A | 12/1995 | Hashino et al. |
| 5,702,727 | A | 12/1997 | Amkraut et al. |
| 5,955,584 | A | 9/1999 | Ditlow et al. |
| 6,375,925 | B1 | 4/2002 | Tsimikas et al. |
| 6,780,605 | B1 | 8/2004 | Frostegård |
| 8,236,562 | B2 | 8/2012 | Schuler et al. |
| 2004/0185039 | A1 | 9/2004 | Kohler et al. |
| 2004/0185514 | A1 | 9/2004 | Frostegård |
| 2004/0185515 | A1 | 9/2004 | Frostegård |
| 2004/0185516 | A1 | 9/2004 | Frostegård |
| 2007/0004910 | A1 | 1/2007 | Sexton et al. |
| 2007/0122419 | A1 | 5/2007 | Witztum et al. |

(Continued)

FOREIGN PATENT DOCUMENTS

| CN | 1471575 A | 1/2004 |
| CN | 1968965 | 5/2007 |
| CN | 102124342 | 7/2011 |

(Continued)

OTHER PUBLICATIONS

Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*

(Continued)

*Primary Examiner* — Sharon X Wen
(74) *Attorney, Agent, or Firm* — Parker Highlander PLLC

(57) ABSTRACT

The present invention relates to an antibody or antibody fragment capable of binding to phosphorylcholine and/or a phosphorylcholine conjugate, wherein the antibody or antibody fragment comprises a variable heavy chain (VH) domain and/or a variable light chain (VL) domain, and wherein—(a) the VH domain comprises an amino acid sequence that includes one, two or three complementarity determining regions (CDRs) selected from the group consisting of: a CDR1 sequence comprising an amino acid sequence having at least 25%, 50%, 75% or 100% sequence identity to the sequence of SEQ ID NO: 17; a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18; and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 19, 20, 21 or 22; and/or (b) the VL domain comprises an amino acid sequence that includes one, two or three complementarity determining regions (CDRs) selected from the group consisting of: a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 23 or 24; a CDR5 sequence comprising an amino acid sequence having at least 14%, 28%, 42%, 57%, 71%, 85% or 100% sequence identity to the sequence of SEQ ID NO: 25; a CDR6 sequence comprising an amino acid sequence having at least 11%, 22%, 33%, 44%, 55%, 66%, 77%, 88% or 100% sequence identity to the sequence of SEQ ID NO: 26.

19 Claims, 7 Drawing Sheets

(56) References Cited

U.S. PATENT DOCUMENTS

| | | |
|---|---|---|
| 2007/0286868 A1 | 12/2007 | De Faire et al. |
| 2009/0258005 A1 | 10/2009 | Gill et al. |

FOREIGN PATENT DOCUMENTS

| | | |
|---|---|---|
| EP | 0257778 | 3/1988 |
| EP | 0466505 | 1/1992 |
| EP | 1095271 | 5/2001 |
| EP | 1335742 | 8/2003 |
| JP | 02188532 | 7/1990 |
| JP | 2008-501636 | 1/2008 |
| JP | 2008-515774 | 5/2008 |
| JP | 2009-517404 | 4/2009 |
| JP | 2009-096346 | 5/2009 |
| JP | 2014-506257 | 3/2014 |
| WO | WO 90/12632 | 11/1990 |
| WO | WO 92/10203 | 6/1992 |
| WO | WO 93/18161 | 9/1993 |
| WO | WO 94/14454 | 7/1994 |
| WO | WO 98/21581 | 5/1998 |
| WO | WO 99/08109 | 2/1999 |
| WO | WO 99/33522 | 7/1999 |
| WO | WO 00/02046 | 1/2000 |
| WO | WO 01/32070 | 5/2001 |
| WO | WO 01/68119 | 9/2001 |
| WO | WO 01/88547 | 11/2001 |
| WO | WO 02/080954 | 10/2002 |
| WO | WO 2004/091520 | 10/2004 |
| WO | WO 2004/106486 | 12/2004 |
| WO | WO 2005/100405 | 10/2005 |
| WO | WO 2006/017538 | 2/2006 |
| WO | WO 2006/110831 | 10/2006 |
| WO | WO 2007/076200 | 7/2007 |
| WO | WO 2010/003602 | 1/2010 |
| WO | WO 2012/010291 | 1/2012 |
| WO | WO 2012/094587 | 7/2012 |
| WO | WO 2013/022968 | 2/2013 |

OTHER PUBLICATIONS

Chang et al., "Monoclonal antibodies against oxidized low-density lipoprotein bind to apoptotic cells and inhibit their phagocytosis by elicited macrophages: evidence that oxidation-specific eptitopes mediate macrophage recognition", *Proceedings of the National Academy of Science*, 96:6353-6358. 1999.

Ewing et al., "Anti-phosphorylcholine IgG antibodies reduce restenosis and vascular inflammation by inhibition of the unfolded protein response in a mouse model of accelerated atherosclerosis", *Circulation*, 122(21): Supplement A14320, 2010.

Frostegård, J., "Low level natural antibodies against phosphorylcholine: a novel risk marker and potential mechanism in atherosclerosis and cardiovascular disease", *Clin Immunol*, 134:47-54, 2010.

Gora et al., "Phospholipolyzed LDL induces an inflammatory response in endothelial cells through endoplasmic reticulum stress signaling", *FASEB J.*, 24(9):3284-97, 2010.

Itabe and Ueda, "Measurement of plasma oxidized low-density lipoprotein and its clinical implications", *J Atheroscler Thromb.*, 14:1-11, 2007.

PCT International Preliminary Report on Patentability, issued in International Application No. PCT/US2012/049990, dated Feb. 11, 2014.

PCT International Preliminary Report on Patentability, issued in International Application No. PCT/EP2012/065505, dated Feb. 11, 2014.

PCT International Search Report and Written Opinion, issued in International Application No. PCT/US2012/049990, dated Dec. 18, 2012.

PCT International Search Report and Written Opinion, issued in International Application No. PCT/EP2012/065505, dated Nov. 7, 2012.

Plückthun et al., "Comparison of the Fv fragments of different phosphorylcholine binding antibodies expressed in *Escherichia coli*", *Annals of the New York Academy of Sciences*, 646:115-124, 1991.

Shaw et al., "Human-derived anti-oxidized LDL autoantibody blocks uptake of oxidized LDL by macrophages and localizes to atherosclerotic lesions in vivo", *Arterioscler Thromb Vasc Biol*, 21:1333-1339, 2001.

Shaw et al., "Natural antibodies with the T15 idiotype may act in atherosclerosis, apoptotic clearance, and protective immunity", *Journal of Clinical Investigation*, 105(12):1731-1740, 2000.

Tabas, "Macrophage death and defective inflammation resolution in atherosclerosis", *Nat Rev Immunol.*, 10:36-46, 2010.

"Single-domain antibody", *Wikepedia, the Free Encyclopedia*, available online at www.wikipedia.org/wiki/Single-domain_antibody, accessed Dec. 6, 2015.

De Faire and Frostegård, "Natural antibodies against phosphorylcholine in cardiovascular disease", *Annals of the New York Academy of Sciences*, 1173(1): 292-300, 2009.

Hoet et al., "Generation of high-affinity human antibodies by combining donor-derived and synthetic complementarity-determining-region diversity", *Nature Biotechnology*, 23(3): 3443-48, 2005.

Hörkkö et al., "Monoclonal autoantibodies specific for oxidized phospholipids or oxidized phospholipid-protein adducts inhibit macrophage uptake of oxidized low-density lipoproteins", *J Clin Invest*, 103(1):117-128, 1999.

Palinski et al., "Cloning of monoclonal autoantibodies to epitopes of oxidized lipoproteins from apolipoprotein e-deficient mice", *J Clin Invest*, 98(3):800-814, 1996.

Schmidt, "Out-licensing: a start-up company perspective", presented at *EuroBio*, Lille, France, Sep. 24, 2009.

Carter, "Potent antibody therapeutics by design", *Nature Reviews Immunology*, 6: 343-357, 2006.

"Announcement of topline results from the GLACIER study", *Press Release*—BioInvent International AB, dated Jul. 11, 2012.

"Assessment and prevention of inflammatory risk in cardiovascular disease," *Athera Biotechnologies*, Company Profile, Oct.-Dec. 2004.

"Biofluids," Product information from Asterand, available online at http://www.asterand.com/Asterand/human_tissues/biofluids.htm, 2009.

"Biofluids," Product information from ProteoGenex, available online at http://www.proteogenex.com/Biorepositoty/Biofluids.html, 2009.

History of Framingham Heart Study, available online at http://www.framinghamheartstudy.org/about/history.html, accessed Dec. 11, 2008.

"Human Derived Products," Product information from Source Bio, Inc., available at http://sourcebioinc.homestad.com/human-derived-products.html, 2008.

"Human Disease State Material and Clinical Samples: Rare Human Plasma," Product information from Sera Lab, available at http://www.seralab.co.uk/index.php?option=com_virtuemart&page=shop.browse&category_id=208&Itemid=42 , 2009.

Abbas et al., "Chapter Three: Antibodies and Antigens", *Cellular and Molecular Immunolgoy*, 2$^{nd}$ Ed., p. 47, 1994. Print.

Albers. Antithrombotic Therapy for Prevention and Treatment of Ischemic Stroke, Journal of Thrombosis and Thrombolysis 12(1), 19-22, 2001.

Bergmark et al., "Patients with early-onset peripheral vascular disease have increased levels of autoantibodies against oxidized LDL," *Arterioscler Thromb Vasc Biol.*, 15:441-445, 1995.

Berliner et al., "Minimally modified low density lipoprotein stimulates monocyte endothelial interactions," *J. Clin Invest.*, 85:1260-1266, 1990.

Binder et al., "Innate and acquired immunity in atherogenesis," *Nature Medicine*, 8(11):1218-1226, 2002.

Binder et al., "Molecular Mimicry between Epitopes of Oxidized LDL and *Streptococcus pneumoniae,*" *Abstracts from American Heart Association Scientific Sessions*, 2005.

(56) References Cited

OTHER PUBLICATIONS

Binder et al., "Pneumococcal vaccination decreases atherosclerotic lesion formation: molecular mimicry between *Streptococcus pneumoniae* and oxidized LDL," *Nature Medicine*, 9(6):736-743, 2003.

Binder, "Defining innate and adaptive immune mechanisms in the atheroprotective effect of immunization with oxidized low-density lipoproteins," *Dissertation Abstracts International*, 63(9):4109, 2005.

Binder, C. J., et al. "Natural antibodies in murine atherosclerosis." Current drug targets 9.3 (2008): 190.

Bochkov et al., "Protective role of phospholipid oxidation products in endotoxin-induced tissue damage," *Nature*, 419:77-81, 2002.

Briles et al., "Anti-phosphorylcholine antibodies of the T15 idiotype are optimally protective against *Streptococcus pneumoniae*," *J. Exp Med.*, 156:1177-1185, 1982.

Byers and Friedman, "Effect of infusions of phosphatides upon the atherosclerotic aorta in situ and as an ocular aortic implant", *J Lipid Res*, 1(4):343-8, 1960.

Caligiuri, Giuseppina, et al. "Phosphorylcholine-targeting immunization reduces atherosclerosis." Journal of the American College of Cardiology 50.6 (2007): 540-546.

Chesebro and Metzger, "Affinity labeling of a phosphorylcholine binding mouse myeloma protein," *Biochemistry*, 11:766-771, 1972.

Chyu et al., "Changes in innate and adaptive humoral immune responses and indices of atherosclerosis in aging," $53^{rd}$ *Annual Scientific Session of the American College of Cardiology*, 2004.

Cooke, The pathophysiology of peripheral arterial disease: rational targets for drug intervention, Vascular Medicine 1997: 2: 227-230.

Crouse et al., Clinical Manifestation of Atherosclerotic Peripheral Arterial Disease and the Role of Cilostazol in Treatment of Intermittent Claudication, J Clin Pharmacol 2002;42:1291-1298.

Dawson et al., Peripheral Arterial Disease: Medical Care and Prevention of Complications, Prev Cardiol. 2002 Summer;5(3):119-30.

Declaration from Hans Henriksnas, in the matter of European patent application No. 05735991.1, dated Jan. 4, 2010.

Declaration from Jan Brundell, in the matter of European patent application No. 05735991.1, dated Jan. 4, 2001.

Dupont, Allison G., Don A. Gabriel, and Mauricio G. Cohen. "Antiplatelet therapies and the role of antiplatelet resistance in acute coronary syndrome." Thrombosis research 124.1 (2009): 6-13.

Emsley and Tyrrell, Inflammation and Infection in Clinical Stroke, Journal of Cerebral Blood Flow & Metabolism 22:1399-1419, 2002.

Faria-Neto, Jose R., et al. "Passive immunization with monoclonal IgM antibodies against phosphorylcholine reduces accelerated vein graft atherosclerosis in apolipoprotein E-null mice." Atherosclerosis 189.1 (2006): 83-90.

Fei et al., "Oxidised LDL modulates immune-activation by an IL-12 dependent mechanism," *Atherosclerosis*, 169:77-85, 2003.

Frasch & Concepcion, "Specificity of human antibodies reactive with pneumococcal C polysaccharide," *Infection and Immunity*, 68:2333-2337, 2000.

Frostegård et al., "Biologically modified LDL increases the adhesive properties of endothelial cells," *Atherosclerosis*, 90:119-126, 1991.

Frostegård et al., "Cytokine expression in advanced human atherosclerotic plaques: dominance of pro-inflammatory (Th1) and macrophage-stimulating cytokines," *Atherosclerosis*, 145:33-43, 1999.

Frostegård et al., "Induction of T-cell activation by oxidized low density lipoprotein," *Arterioscler Thromb.*, 12:461-467, 1992.

Frostegård et al., "Oxidized low density lipoprotein induces differentiation and adhesion of human monocytes and the monocytic cell line U937," *Proc. Natl. Acad. Sci. USA*, 87:904-908, 1990.

Frostegård et al., "Platelet-activating factor and oxidized LDL induce immune activation by a common mechanism," *Arterioscler Thromb Vasc Biol.*, 17:963-968, 1997.

Frostegård, "Autoimmunity, oxidized LDL and cardiovascular disease," *Autoimmunity Reviews*, 1:233-237, 2002.

Gearhart et al., "Heterogeneity of the BALB/c antiphosphorylcholine antibody response at the precursor cell level," *Journal of Experimental Medicine*, 141(1):56-71, 1975.

Gearhart, Patricia J., et al. "IgG antibodies to phosphorylcholine exhibit more diversity than their IgM counterparts." Nature 291. 5810 (1981): 29-34.

Genbank, Accession No. J00253.1, Dated May 4, 2000, www.ncbi.nlm.nih.gov.

Hanson, "Inflammation, atherosclerosis, and coronary artery disease," *The New England Journal of Medicine*, 352(16):1685-1695, 2005.

Harnett and Harnett, "Immunomodulation by filarial nematode phosphorylcholine-containing glycoproteins," In: *Parasitic Nematodes*, CABI Publishing, Wallingford, UK, 399-414, 2001.

Harnett and Harnett, "Phosphorylcholine: friend or foe of the immune system," *Immunol. Today*, 20:125-129, 1999.

Heery et al., "Oxidatively modified LDL contains phospholipids with platelet-activating factor-like activity and stimulates the growth of smooth muscle cells," *J. Clin. Invest.*, 96:2322-2330, 1995.

Hulthe et al., "Antibodies to oxidized LDL in relation to carotid atherosclerosis, cell adhesion molecules, and phospholipase $A_2$," *Arterioscler Thromb Vasc Biol.*, 21:269-274, 2001.

Humphries and Morgan, Genetic risk factors for stroke and carotid atherosclerosis: insights into pathophysiology from candidate gene approaches, Lancet Neurol 2004; 3: 227-36.

Kameyama et al, "Convenient plasmid vectors for construction of chimeric mouse/human antibodies," *FEBS Letters*, 244(2):301-306, 1989.

Karvonen et al., "Immunoglobulin M type of autoantibodies to oxidized low-density lipoprotein has an inverse relation to carotid artery atherosclerosis," *Circulation*, 108:2107-2112, 2003.

Kearney, "Immune recognition of OxLDL in atherosclerosis," *Journal of Clinical Investigation*, 105(12):1683-1685, 2000.

Kim et al., "I-PLA2 activation during apoptosis promotes the exposure of membrane lysophosphatidylcholine leading to binding by natural immunoglobulin M antibodies and complement activation," *J. Exp. Med.*, 196(5):655-665, 2002.

Kita et al., "Role of oxidized LDL in atherosclerosis," *Annals New York Academy of Sciences*, 947:199-205. Discussion 205-206, 2001.

Kitagawa et al., "Involvement of ICAM-1 in the progression of atherosclerosis in APOE-knockout mice," *Atherosclerosis*, 160(2):305-10, 2002.

Knoflach et al., "Immunity to heat shock proteins and atherosclerosis," In: *Heat Shock Proteins and Inflammation*, Birkhaeuser Verlag, Basel, Switzerland, 159-173, 2003.

La Belle and Krauss, "Differences in carbohydrate content of low density lipoproteins associated with low density lipoprotein subclass patterns", *Journal of Lipid Research*, 31:1577-1588, 1990.

Lawson and Wolf, "ICAM-1 signaling in endothelial cells," *Pharmacological Reports*, 61:22-32, 2009.

Libby, Peter, et al. "Macrophages and atherosclerotic plaque stability." Current opinion in lipidology 7.5 (1996): 330-335.

Lim et al., "One-step 2-minute test to detect typhoid-specific antibodies based on particle separation in tubes," *Journal of Clinical Microbiology*, 36(8):2271-2278, 1998.

Malmö Diet and Cancer Study, available online at http://www.biobanks.se/malmodiet.htm, accessed Dec. 11, 2008.

Malmö Diet Cancer, 2008.

Morrison et al., "Chimeric human antibody molecules: mouse antigen-binding domains with human constant region domains", *Proc. Natl. Acad. Sci.*, 81:6851-6855, 1984.

Padilla et al., "Levels of natural IgM antibodies against phosphorylcholine in healthy individuals and in patients undergoing isolated limb perfusion," *Journal of Immunological Methods*, 293:1-11, 2004.

Palinski et al., "Immunization of low density lipoprotein (LDL) receptor-deficient rabbits with homologous malondialdehyde-modified LDL reduces atherogenesis," *Proc. Natl. Acad. Sci. USA*, 92:821-825, 1995.

Pearsall, Judy, ed. "Monoclonal Antibody", *The New Oxford Dictionary of English*, p. 1195, 2001.

(56) References Cited

OTHER PUBLICATIONS

Pettersson et al. "A fully human monoclonal IgG phosphorylcholine antibody prevents accelerated atherosclerosis in mice" (Poster), American Heart Association Meeting, 2011.
Pockley et at, "Serum heat shock protein 70 levels predict the development of atherosclerosis in subjects with established hypertension," *Hypertension*, 42:235-238, 2003.
Purkall et al., "Opsonization of *Actinobacillus actinomycetemcomitans* by immunoglobulin G antibody reactive with phosphorylcholine," *Infection and Immunity*, 70(11):6485-6488, 2002.
Reape, Theresa J., and Pieter HE Groot. "Chemokines and atherosclerosis." Atherosclerosis 147.2 (1999): 213-225.
Rose and Afanasyeva, "Autoimmunity: busting the atherosclerotic plaque," *Nature medicine*, 9(6):641-642, 2003.
Salonen et at, "Autoantibody against oxidised LDL and progression of carotid atherosclerosis," *The Lancet*, 339(8798):883-887, 1992.
Schenkein et al., "Antiphosphorylcholine antibody levels are elevated in humans with periodontal diseases," *Infection and Immunity*, 67(9):4814-4818, 1999.
Schenkein et al., "Phosphorylcholine-dependent cross-reactivity between dental plaque bacteria and oxidized low-density lipoproteins," *Infection and Immunity*, 69(11):6612-6617, 2001.
Segal, David M., et al. "The three-dimensional structure of a phosphorylcholine-binding mouse immunoglobulin Fab and the nature of the antigen binding site." Proceedings of the National Academy of Sciences 71.11 (1974): 4298-4302.
Shaw et al., "The autoreactivity of anti-phosphorylcholine antibodies for atherosclerosis-associated neo-antigens and apoptotic cells," *The Journal of Immunology*, 170(12):6151-6157, 2003.
Shoji et al., "Inverse relationship between circulating oxidized low density lipoprotein (oxLDL) and anti-oxLDL antibody levels in healthy subjects," *Atherosclerosis*, 148(1):171-177, 2000.
Simpson and Beachey, "Adherence of group A *streptococci* to fibronectin on oral epithelial cells," *Infection and Immunity*, 39(1):275-279, 1983.
Spira et al., "T15 PC binding monoclonal antibodies retain specificity when they switch from IgM to IgG," *Journal of Immunology*, 140(8):2675-2680, 1988.
Stemme et al., "T lymphocytes from human atherosclerotic plaques recognize oxidized low density lipoprotein," *Proc. Natl. Acad. Sci. USA*, 92:3893-3897, 1995.
Subbanagounder et al., "Evidence that phospholipid oxidation products and/or platelet-activating factor play an important role in early atherogenesis: in vitro and in vivo inhibition by WEB 2086," *Circa Res.*, 85:311-318, 1999.
Svenungsson et al., "Risk factors for cardiovascular disease in systemic lupus erythematosus," *Circulation*, 104:1887-1893, 2001.
Takeoka et at, "Function of fibrinogen gamma-chain dodecapeptide-conjugated latex beads under flow," *Biochem. Biophys. Res. Commun.*, 312(3):773-779, 2003.
Tegos et al., The Genesis of Atherosclerosis and Risk Factors: A Review, Angiology 52:89-98, 2001.
Todd et al., "Immunologic memory to phosphorylcholine VI. Heterogeneity in light chain gene expression," *European Journal of Immunology*, 15(2):177-183, 1985.
Trolle et al., "Intranasal immunization with protein-linked phosphorylcholine protects mise against a lethal intranasal challenge with *Streptococcus pneumoniae*," *Vaccine*, 18(26):2991-2998, 2000.
Wu et al., "Autoantibodies to OxLDL are decreased in individuals with borderline hypertension," *Hypertension*, 33:53-59, 1999.
Xu et al., "Induction of Arteriosclerosis in normocholesterolemic rabbits by immunization with heat shock protein 65," *Arterioscler. Thromb.*, 12:789-799, 1992.
Zanchetti et al., "Calcium antagonist lacidipine slows down progression of asymptomatic carotid atherosclerosis: principal results of the European Lacidipine Study on Atherosclerosis (ELSA), a randomized, double-blind, long-term trial," *Circulation*, 106:2422-2427, 2002.
Zanchetti et al., "Risk factors associated with alterations in carotid intima-media thickness in hypertension: baseline data from the European Lacidipine Study on Atherosclerosis," *J. Hypertension*, 16:949-961, 1998.

\* cited by examiner

PBS

HuIgG1 anti-strep A2

M99-B05

SEQUENCE LISTING

```
<160> NUMBER OF SEQ ID NOS: 29

<210> SEQ ID NO 1
<211> LENGTH: 131
<212> TYPE: PRT
<213> ORGANISM: Artificial Sequence
<220> FEATURE:
<223> OTHER INFORMATION: Synthetic polypeptide (VH domain of X19-A05
      antibody)

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met His Trp Val Arg Gln Ala Pro Gly Lys Gly Leu Glu Trp Val
        35                  40                  45

Ser Tyr Ile Ser Pro Ser Gly Gly Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Phe Arg Ser Val Cys Ser Asn Ala Val Cys Arg Pro
            100                 105                 110

Thr Ala Tyr Asp Ala Phe Asp Ile Trp Gly Gln Gly Thr Met Val Thr
        115                 120                 125

Val Ser Ser
    130

<210> SEQ ID NO 2
<211> LENGTH: 113
<212> TYPE: PRT
<213> ORGANISM: Artificial Sequence
<220> FEATURE:
<223> OTHER INFORMATION: Synthetic polypeptide (VL domain of X19-A05
      antibody)

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Gln
            20                  25                  30
```

Ser Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Phe Asn Ala Pro Arg Thr Phe Gly Gln Gly Thr Lys Val Glu Ile
                100                 105                 110

Lys

<210> SEQ ID NO 3
<211> LENGTH: 130
<212> TYPE: PRT
<213> ORGANISM: Artificial Sequence
<220> FEATURE:
<223> OTHER INFORMATION: Synthetic polypeptide (VH domain of M99-B05
      antibody)

<400> SEQUENCE: 3

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Ser Gly Tyr Trp
                20                  25                  30

Met His Trp Val Arg Gln Ala Pro Gly Lys Gly Leu Glu Trp Val Ser
            35                  40                  45

Tyr Ile Ser Pro Ser Gly Gly Thr His Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Val Arg Phe Arg Ser Val Cys Ser Asn Gly Val Cys Arg Pro Thr
                100                 105                 110

Ala Tyr Asp Ala Phe Asp Ile Trp Gly Gln Gly Thr Ala Val Thr Val
            115                 120                 125

Ser Ser
    130

<210> SEQ ID NO 4
<211> LENGTH: 114
<212> TYPE: PRT
<213> ORGANISM: Artificial Sequence
<220> FEATURE:
<223> OTHER INFORMATION: Synthetic polypeptide (VL domain of M99-B05
      antibody)

<400> SEQUENCE: 4

Gln Asp Ile Gln Met Thr Gln Ser Pro Asp Ser Leu Ala Val Ser Leu
 1               5                  10                  15

Gly Glu Arg Ala Thr Ile Asn Cys Lys Ser Ser Gln Ser Val Phe Tyr
                20                  25                  30

Asn Ser Asn Lys Lys Asn Tyr Leu Ala Trp Tyr Gln Gln Lys Ala Gly
            35                  40                  45

Gln Pro Pro Lys Leu Leu Ile His Trp Ala Ser Thr Arg Glu Ser Gly
 50                  55                  60

Val Pro Asp Arg Phe Ser Gly Ser Gly Ser Gly Thr Asp Phe Thr Leu

```
65                  70                  75                  80
Thr Ile Ser Asn Leu Gln Ala Glu Asp Val Ala Leu Tyr Tyr Cys Gln
                85                  90                  95
Gln Tyr Phe Asn Ala Pro Arg Thr Phe Gly Gln Gly Thr Lys Val Glu
            100                 105                 110
Ile Lys

<210> SEQ ID NO 5
<211> LENGTH: 130
<212> TYPE: PRT
<213> ORGANISM: Artificial Sequence
<220> FEATURE:
<223> OTHER INFORMATION: Synthetic polypeptide (VH domain of X19-A01
      antibody)

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Gly Tyr Trp
            20                  25                  30

Met His Trp Val Arg Gln Ala Pro Gly Lys Gly Leu Glu Trp Val Ser
        35                  40                  45

Tyr Ile Ser Pro Ser Gly Gly Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Arg Phe Arg Ser Val Cys Ser Asn Gly Val Cys Arg Pro Thr
            100                 105                 110

Ala Tyr Asp Ala Phe Asp Ile Trp Gly Gln Gly Thr Ala Val Thr Val
        115                 120                 125

Ser Ser
    130

<210> SEQ ID NO 6
<211> LENGTH: 113
<212> TYPE: PRT
<213> ORGANISM: Artificial Sequence
<220> FEATURE:
<223> OTHER INFORMATION: Synthetic polypeptide (VL domain of X19-A01
      antibody)

<400> SEQUENCE: 6

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Asn
            20                  25                  30

Ser Asn Lys Lys Asn Tyr Leu Ala Trp Tyr Gln Gln Lys Ala Gly Gln
        35                  40                  45

Pro Pro Lys Leu Leu Ile His Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Asn Leu Gln Ala Glu Asp Val Ala Leu Tyr Tyr Cys Gln Gln
                85                  90                  95

Tyr Phe Asn Ala Pro Arg Thr Phe Gly Gln Gly Thr Lys Val Glu Ile
            100                 105                 110
```

Lys

```
<210> SEQ ID NO 7
<211> LENGTH: 130
<212> TYPE: PRT
<213> ORGANISM: Artificial Sequence
<220> FEATURE:
<223> OTHER INFORMATION: Synthetic polypeptide (VH domain of X19-A03
      antibody)

<400> SEQUENCE: 7
```

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1 | | | | 5 | | | | | 10 | | | | | 15 | |

| Ser | Leu | Arg | Leu | Ser | Cys | Ala | Ala | Ser | Gly | Phe | Thr | Ser | Gly | Tyr | Trp |
| | | 20 | | | | | 25 | | | | | 30 | | | |

| Met | His | Trp | Val | Arg | Gln | Ala | Pro | Gly | Lys | Gly | Leu | Glu | Trp | Val | Ser |
| | | 35 | | | | | 40 | | | | | 45 | | | |

| Tyr | Ile | Ser | Pro | Ser | Gly | Gly | Thr | His | Tyr | Ala | Asp | Ser | Val | Lys |
| 50 | | | | | 55 | | | | | 60 | | | | | |

| Gly | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |

| Arg | Val | Arg | Phe | Arg | Ser | Val | Cys | Ser | Asn | Ala | Val | Cys | Arg | Pro | Thr |
| | | | | 100 | | | | | 105 | | | | | 110 | |

| Ala | Tyr | Asp | Ala | Phe | Asp | Ile | Trp | Gly | Gln | Gly | Thr | Met | Val | Thr | Val |
| | | | 115 | | | | | 120 | | | | | 125 | | |

| Ser | Ser |
| | 130 |

```
<210> SEQ ID NO 8
<211> LENGTH: 113
<212> TYPE: PRT
<213> ORGANISM: Artificial Sequence
<220> FEATURE:
<223> OTHER INFORMATION: Synthetic polypeptide (VL domain of X19-A03
      antibody)

<400> SEQUENCE: 8
```

| Asp | Ile | Val | Met | Thr | Gln | Ser | Pro | Asp | Ser | Leu | Ala | Val | Ser | Leu | Gly |
|-----|-----|-----|-----|-----|-----|-----|-----|-----|-----|-----|-----|-----|-----|-----|-----|
| 1 | | | | 5 | | | | | 10 | | | | | 15 | |

| Glu | Arg | Ala | Thr | Ile | Asn | Cys | Lys | Ser | Ser | Gln | Ser | Val | Phe | Tyr | Gln |
| | | | 20 | | | | | 25 | | | | | 30 | | |

| Ser | Asn | Lys | Lys | Asn | Tyr | Leu | Ala | Trp | Tyr | Gln | Gln | Lys | Pro | Gly | Gln |
| | | 35 | | | | | 40 | | | | | 45 | | | |

| Pro | Pro | Lys | Leu | Leu | Ile | Tyr | Trp | Ala | Ser | Thr | Arg | Glu | Ser | Gly | Val |
| | 50 | | | | | 55 | | | | | 60 | | | | |

| Pro | Asp | Arg | Phe | Ser | Gly | Ser | Gly | Ser | Gly | Thr | Asp | Phe | Thr | Leu | Thr |
| 65 | | | | | 70 | | | | | 75 | | | | | 80 |

| Ile | Ser | Ser | Leu | Gln | Ala | Glu | Asp | Val | Ala | Val | Tyr | Tyr | Cys | Gln | Gln |
| | | | | 85 | | | | | 90 | | | | | 95 | |

| Tyr | Phe | Asn | Ala | Pro | Arg | Thr | Phe | Gly | Gln | Gly | Thr | Lys | Val | Glu | Ile |
| | | | 100 | | | | | 105 | | | | | 110 | | |

| Lys |

```
<210> SEQ ID NO 9
<211> LENGTH: 130
<212> TYPE: PRT
```

-continued

<213> ORGANISM: Artificial Sequence
<220> FEATURE:
<223> OTHER INFORMATION: Synthetic polypeptide (VH domain of X19-A07 antibody)

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Gly Tyr Trp
            20                  25                  30

Met His Trp Val Arg Gln Ala Pro Gly Lys Gly Leu Glu Trp Val Ser
        35                  40                  45

Tyr Ile Ser Pro Ser Gly Gly Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Arg Phe Arg Ser Val Cys Ser Asn Gly Val Cys Arg Pro Thr
            100                 105                 110

Ala Tyr Asp Ala Phe Asp Ile Trp Gly Gln Gly Thr Met Val Thr Val
        115                 120                 125

Ser Ser
130

<210> SEQ ID NO 10
<211> LENGTH: 113
<212> TYPE: PRT
<213> ORGANISM: Artificial Sequence
<220> FEATURE:
<223> OTHER INFORMATION: Synthetic polypeptide (VL domain of X19-A07 antibody)

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Asn
            20                  25                  30

Ser Asn Lys Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Asn Ala Pro Arg Thr Phe Gly Gln Gly Thr Lys Val Glu Ile
            100                 105                 110

Lys

<210> SEQ ID NO 11
<211> LENGTH: 131
<212> TYPE: PRT
<213> ORGANISM: Artificial Sequence
<220> FEATURE:
<223> OTHER INFORMATION: Synthetic polypeptide (VH domain of X19-A09 antibody)

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met His Trp Val Arg Gln Ala Pro Gly Lys Gly Leu Glu Trp Val
            35                  40                  45

Ser Tyr Ile Ser Pro Ser Gly Gly Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Phe Arg Ser Val Cys Ser Asn Gly Val Cys Arg Pro
            100                 105                 110

Thr Ala Tyr Asp Ala Phe Asp Ile Trp Gly Gln Gly Thr Met Val Thr
            115                 120                 125

Val Ser Ser
    130

<210> SEQ ID NO 12
<211> LENGTH: 113
<212> TYPE: PRT
<213> ORGANISM: Artificial Sequence
<220> FEATURE:
<223> OTHER INFORMATION: Synthetic polypeptide (VL domain of X19-A09
      antibody)

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Asn
            20                  25                  30

Ser Asn Lys Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Asn Ala Pro Arg Thr Phe Gly Gln Gly Thr Lys Val Glu Ile
            100                 105                 110

Lys

<210> SEQ ID NO 13
<211> LENGTH: 130
<212> TYPE: PRT
<213> ORGANISM: Artificial Sequence
<220> FEATURE:
<223> OTHER INFORMATION: Synthetic polypeptide (VH domain of X19-A11
      antibody)

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Gly Tyr Trp
            20                  25                  30

Met His Trp Val Arg Gln Ala Pro Gly Lys Gly Leu Glu Trp Val Ser

```
                35                  40                  45
Tyr Ile Ser Pro Ser Gly Gly Thr His Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Val Arg Phe Arg Ser Val Ser Asn Gly Val Ser Arg Pro Thr
            100                 105                 110

Ala Tyr Asp Ala Phe Asp Ile Trp Gly Gln Gly Thr Ala Val Thr Val
            115                 120                 125

Ser Ser
    130

<210> SEQ ID NO 14
<211> LENGTH: 113
<212> TYPE: PRT
<213> ORGANISM: Artificial Sequence
<220> FEATURE:
<223> OTHER INFORMATION: Synthetic polypeptide (VL domain of the X19-A11
      antibody)

<400> SEQUENCE: 14

Asp Ile Gln Met Thr Gln Ser Pro Asp Ser Leu Ala Val Ser Leu Gly
 1               5                  10                  15

Glu Arg Ala Thr Ile Asn Cys Lys Ser Ser Gln Ser Val Phe Tyr Asn
             20                  25                  30

Ser Asn Lys Lys Asn Tyr Leu Ala Trp Tyr Gln Gln Lys Ala Gly Gln
         35                  40                  45

Pro Pro Lys Leu Leu Ile His Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Asn Leu Gln Ala Glu Asp Val Ala Leu Tyr Tyr Cys Gln Gln
                 85                  90                  95

Tyr Phe Asn Ala Pro Arg Thr Phe Gly Gln Gly Thr Lys Val Glu Ile
            100                 105                 110

Lys

<210> SEQ ID NO 15
<211> LENGTH: 130
<212> TYPE: PRT
<213> ORGANISM: Artificial Sequence
<220> FEATURE:
<223> OTHER INFORMATION: Synthetic polypeptide (VH domain of X19-C01
      antibody)

<400> SEQUENCE: 15

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Ser Gly Tyr Trp
             20                  25                  30

Met His Trp Val Arg Gln Ala Pro Gly Lys Gly Leu Glu Trp Val Ser
         35                  40                  45

Tyr Ile Ser Pro Ser Gly Gly Thr His Tyr Ala Asp Ser Val Lys
         50                  55                  60

Gly Arg Phe Thr Ile Ser Arg Asp Asn Ser Lys Asn Thr Leu Tyr Leu
 65                  70                  75                  80
```

```
Gln Met Asn Ser Leu Arg Ala Glu Asp Thr Ala Val Tyr Tyr Cys Ala
                85                  90                  95

Arg Val Arg Phe Arg Ser Val Ser Ser Asn Ala Val Ser Arg Pro Thr
            100                 105                 110

Ala Tyr Asp Ala Phe Asp Ile Trp Gly Gln Gly Thr Met Val Thr Val
        115                 120                 125

Ser Ser
    130

<210> SEQ ID NO 16
<211> LENGTH: 113
<212> TYPE: PRT
<213> ORGANISM: Artificial Sequence
<220> FEATURE:
<223> OTHER INFORMATION: Synthetic polypeptide (VL domain of the X19-C01
      antibody)

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Gln
            20                  25                  30

Ser Asn Lys Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Asn Ala Pro Arg Thr Phe Gly Gln Gly Thr Lys Val Glu Ile
            100                 105                 110

Lys

<210> SEQ ID NO 17
<211> LENGTH: 4
<212> TYPE: PRT
<213> ORGANISM: Artificial Sequence
<220> FEATURE:
<223> OTHER INFORMATION: Synthetic peptide (CDR1 of the VH domain of
      X19-A05, M99-B05, X19-A01, X19-A03, X19-A07, X19-A09, X19-A11 and
      X19-C01 antibodies)

<400> SEQUENCE: 17

Gly Tyr Trp Met
1

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide (CDR2 of the VH domain of
      X19-A05, M99-B05, X19-A01, X19-A03, X19-A07, X19-A09, X19-A11 and
      X19-C01 antibodies)

<400> SEQUENCE: 18

Tyr Ile Ser Pro Ser Gly Gly Thr His Tyr Ala Asp Ser Val Lys
1               5                   10                  15

Gly
```

```
<210> SEQ ID NO 19
<211> LENGTH: 22
<212> TYPE: PRT
<213> ORGANISM: Artificial Sequence
<220> FEATURE:
<223> OTHER INFORMATION: Synthetic peptide (CDR3 of the VH domain of
      X19-A05 and X19-A03 antibodies)

<400> SEQUENCE: 19

Val Arg Phe Arg Ser Val Cys Ser Asn Ala Val Cys Arg Pro Thr Ala
1               5                   10                  15

Tyr Asp Ala Phe Asp Ile
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic polypeptide (CDR3 of the VH domain of
      M99-B05, X19-A01, X19-A07 and X19-A09 antibodies)

<400> SEQUENCE: 20

Val Arg Phe Arg Ser Val Cys Ser Asn Gly Val Cys Arg Pro Thr Ala
1               5                   10                  15

Tyr Asp Ala Phe Asp Ile
            20

<210> SEQ ID NO 21
<211> LENGTH: 22
<212> TYPE: PRT
<213> ORGANISM: Artificial Sequence
<220> FEATURE:
<223> OTHER INFORMATION: Synthetic peptide (CDR3 of the VH domain of
      X19-A11 antibody)

<400> SEQUENCE: 21

Val Arg Phe Arg Ser Val Ser Ser Asn Gly Val Ser Arg Pro Thr Ala
1               5                   10                  15

Tyr Asp Ala Phe Asp Ile
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic peptide (CDR3 of the VH domain of
      X19-C01 antibody)

<400> SEQUENCE: 22

Val Arg Phe Arg Ser Val Ser Ser Asn Ala Val Ser Arg Pro Thr Ala
1               5                   10                  15

Tyr Asp Ala Phe Asp Ile
            20

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide (CDR4 of the VL domain of
      X19-A05, X19-A03 and X19-C01 antibodies)

<400> SEQUENCE: 23
```

Lys Ser Ser Gln Ser Val Phe Tyr Gln Ser Asn Lys Lys Asn Tyr Leu
1               5                   10                  15

Ala

<210> SEQ ID NO 24
<211> LENGTH: 17
<212> TYPE: PRT
<213> ORGANISM: Artificial Sequence
<220> FEATURE:
<223> OTHER INFORMATION: Synthetic peptide (CDR4 of the VL domain of
      M99-B05, X19-A01, X19-A07, X19-A09 and X19-A11 antibodies)

<400> SEQUENCE: 24

Lys Ser Ser Gln Ser Val Phe Tyr Asn Ser Asn Lys Lys Asn Tyr Leu
1               5                   10                  15

Ala

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide (CDR5 of the VL domain of
      X19-A05, M99-B05, X19-A01, X19-A03, X19-A07, X19-A09, X19-A11 and
      X19-C01 antibodies)

<400> SEQUENCE: 25

Trp Ala Ser Thr Arg Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide (CDR6 of the VL domain of
      X19-A05, M99-B05, X19-A01, X19-A03, X19-A07, X19-A09, X19-A11 and
      X19-C01 antibodies)

<400> SEQUENCE: 26

Gln Gln Tyr Phe Asn Ala Pro Arg Thr
1               5

<210> SEQ ID NO 27
<211> LENGTH: 330
<212> TYPE: PRT
<213> ORGANISM: Artificial Sequence
<220> FEATURE:
<223> OTHER INFORMATION: Synthetic polypeptide (CH region of M99-B05
      antibody)

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 329
<212> TYPE: PRT
<213> ORGANISM: Artificial Sequence
<220> FEATURE:
<223> OTHER INFORMATION: Synthetic polypeptide (CH region of X19-A05
      antibody)

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
                  115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 29
<211> LENGTH: 107
<212> TYPE: PRT
<213> ORGANISM: Artificial Sequence
<220> FEATURE:
<223> OTHER INFORMATION: Synthetic polypeptide (VL region of M99-B05
      and X19-A05 antibodies)

<400> SEQUENCE: 29

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

ANTIBODIES AGAINST PHOSPHORYLCHOLINE

The application is a national phase application under 35 U.S.C. §371 of International Application No. PCT/EP2012/065505, filed Aug. 8, 2012, which claims priority to U.S. Provisional Patent Application No. 61/521,593, filed Aug. 9, 2011. The entire text of each of the above referenced disclosures is specifically incorporated herein by reference.

FIELD OF THE INVENTION

The present invention relates to new antibodies with binding to phosphorylcholine (PC) and/or PC conjugates and having surprisingly effective in vivo properties.

BACKGROUND TO THE INVENTION

The listing or discussion of an apparently prior-published document in this specification should not necessarily be taken as an acknowledgement that the document is part of the state of the art or is common general knowledge.

Despite the available treatment options available for cardiovascular disease, acute coronary syndrome (ACS) is the leading cause of death in the industrialized world. ACS occurs as a result of thrombus formation within the lumen of a coronary artery, which is associated with chronic inflammation within the wall of the artery. Arterial inflammation is initiated by the formation of a lipid core and infiltration of inflammatory cells leading to plaque formation. Unstable plaques contain a substantial necrotic core and apoptotic cells that disrupt the endothelium and can lead to plaque rupture exposing of underlying collagen, von Willebrand factor (vWF), tissue factor, lipids and smooth muscle allowing initiation of platelet adhesion, activation, and aggregation (Libby et al. 1996. *Macrophages and atherosclerotic plaque stability. Curr Opin Lipidol* 7, 330-335). ACS is treated with a combination of anti-platelet therapies, cholesterol lowering medications (e.g. statins), anti-coagulants, as well as surgical recanalization through percutaneous coronary intervention (PCI) and implantation of stents.

Anti-platelet therapies such as COX-1 inhibitors (e.g. aspirin), ADP receptor antagonists (e.g. Ticlopedine and clopidogrel), and glycoprotein IIb/IIIa receptor antagonists have been shown to reduce the incidence of major adverse coronary events (MACE) in a number of different clinical trials (Dupont et al-2009-*Antiplatelet therapies and the role of antiplatelet resistance in acute coronary syndrome. Thromb Res* 124, 6-13). However, a proportion of patients on long-term anti-platelet therapy continue to have cardiovascular events. Moreover, chronic prevention therapy may take up to two years to show maximum beneficial effects, and many patients are then still at high risk for recurrent disease. There is a period of up to 6-12 months after a myocardial infarction that the patient is susceptible to further MACE, frequently due to re-occlusion due to restenosis (Tabas. 2010. *Macrophage death and defective inflammation resolution in atherosclerosis. Nat Rev Immunol* 10, 36-46).

Consequently, there is a significant need for treatments directed specifically at preventing further plaque progression and promoting plaque regression could substantially lower events during this period.

Phosphorylcholine, a polar head group on certain phospholipids, has been extensively implicated in cardiovascular disease. Reactive oxygen species generated during coronary inflammation causes the oxidation of low density lipoprotein (LDL) to generate oxidized LDL (oxLDL). In fact, cardiovascular diseases (CVD) such as atherosclerosis, unstabile angina, or acute coronary syndrome have been shown to be associated with elevated plasma levels of oxLDL (Itabe and Ueda. 2007. *Measurement of plasma oxidized low-density lipoprotein and its clinical implications. J Atheroscler Thromb* 14, 1-11). LDL is a circulating lipoprotein particle that contains lipids with a PC polar head group and an apoB100 protein.

During oxidation of LDL PC containing neo-epitopes that are not present on unmodified LDL, are generated. Newly exposed PC on oxLDL is recognized by scavenger receptors on macrophages, such as CD36, and the resulting macrophage-engulfed oxLDL proceeds towards the formation of pro-inflammatory foam cells in the vessel wall. Oxidized LDL is also recognized by receptors on endothelial cell surfaces and has been reported to stimulate a range of responses including endothelial dysfunction, apoptosis, and the unfolded protein response (Gora et al. 2010. *Phospholipolyzed LDL induces an inflammatory response in endothelial cells through endoplasmic reticulum stress signaling. FASEB J* 24(9):3284-97). PC neo-epitopes are also exposed on LDL following modification with phospholipase A2 or amine reactive disease metabolites, such as aldehydes generated from the oxidation of glycated proteins. These alternately modified LDL particles are also pro-inflammatory factors in CVD.

Antibodies towards phosphorylcholine (PC) have been shown to bind oxidized, or otherwise modified, LDL and block the pro-inflammatory activity of oxLDL in in vivo models or in vitro studies (Shaw et al. 2000. *Natural antibodies with the T15 idiotype may act in atherosclerosis, apoptotic clearance, and protective immunity. J Clin Invest* 105, 1731-1740; Shaw et al. 2001. *Human-derived anti-oxidized LDL autoantibody blocks uptake of oxidized LDL by macrophages and localizes to atherosclerotic lesions in vivo. Arterioscler Thromb Vasc Biol* 21, 1333-1339.

Furthermore, an examination of clinical data has demonstrated that low levels of natural IgM anti-PC antibodies are associated with an increased risk of MACE in ACS patients (Frostegard, J. 2010. *Low level natural antibodies against phosphorylcholine: a novel risk marker and potential mechanism in atherosclerosis and cardiovascular disease. Clin Immunol* 134, 47-54).

Accordingly, there is a need for anti-PC antibody molecules that can be effectively used in therapy, particularly fully human anti-PC antibodies suitable for human therapy. To the applicant's knowledge, to date the art has failed to provide therapeutically efficacious human anti-PC antibodies. The identification of such antibodies has been hampered by the fact that in vitro screening methods for human antibodies with anti-PC binding activity are poor predictors of in vivo therapeutic activity.

In view of this, there is a need in the art for human anti-PC antibody molecules that provide effective and advantageous properties when used in in vivo systems, in particular when administered to humans for therapy.

DESCRIPTION OF THE INVENTION

The present application describes the production and testing of new antibodies and antibody fragments comprising novel antigen-binding regions capable of binding to phosphorylcholine and/or phosphorylcholine conjugates.

In a first aspect, the present invention provides an antibody or antibody fragment capable of binding to phosphorylcholine and/or a phosphorylcholine conjugate, wherein the antibody or antibody fragment comprises a variable heavy chain (VH) domain and/or a variable light chain (VL) domain, and wherein—
(a) the VH domain comprises an amino acid sequence that includes one, two or preferably three complementarity determining regions (CDRs) selected from the group consisting of:
   a CDR1 sequence comprising an amino acid sequence having at least 25%, 50%, 75% or 100% sequence identity to the sequence of SEQ ID NO: 17;
   a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18; and
   a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 19, 20, 21 or 22; and/or
(b) the VL domain comprises an amino acid sequence that includes one, two or preferably three complementarity determining regions (CDRs) selected from the group consisting of:
   a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 23 or 24;
   a CDR5 sequence comprising an amino acid sequence having at least 14%, 28%, 42%, 57%, 71%, 85% or 100% sequence identity to the sequence of SEQ ID NO: 25;
   a CDR6 sequence comprising an amino acid sequence having at least 11%, 22%, 33%, 44%, 55%, 66%, 77%, 88% or 100% sequence identity to the sequence of SEQ ID NO: 26.

In one embodiment according to the first aspect of the present invention, the antibody or antibody fragment comprises a VH domain that comprises an amino acid sequence that includes a CDR1 sequence, a CDR2 and a CDR3 sequence as defined above, and/or a VL domain that comprises an amino acid sequence that includes a CDR4 sequence, a CDR5 and a CDR6 sequence as defined above.

In a further embodiment of the first aspect of the present invention, the antibody or antibody fragment comprises—
   a VH domain that comprises an amino acid sequence that includes all three of the CDR1, CDR2 and CDR3 sequences present in an amino acid sequence selected from the group consisting of SEQ ID NOs: 1, 3, 5, 7, 9, 11, 13, or 15 or an amino acid sequence having at least 80%, 85%, 90%, or 95% sequence identity to an amino acid sequence of any of SEQ ID NOs: 1, 3, 5, 7, 9, 11, 13, or 15; and/or
   a VL domain that comprises an amino acid sequence that includes all three of the CDR4, CDR5 and CDR6 sequences present in an amino acid sequence selected from the group consisting of SEQ ID NOs: 2, 4, 6, 8, 10, 12, 14, or 16 or an amino acid sequence having at least 80%, 85%, 90%, or 95% sequence identity to an amino acid sequence of any of SEQ ID NOs: 2, 4, 6, 8, 10, 12, 14, or 16.

In a further embodiment of the first aspect of the present invention, the antibody or antibody fragment comprises a variable heavy chain (VH) domain and/or a variable light chain (VL) domain, wherein— the VH domain comprises an amino acid sequence selected from the group consisting of SEQ ID NOs: 1, 3, 5, 7, 9, 11, 13, or 15 or an amino acid sequence having at least 50%, 60%, 70%, 80%, 85%, 90%, or 95% sequence identity to an amino acid sequence of any of SEQ ID NOs: 1, 3, 5, 7, 9, 11, 13, or 15; and
the VL domain comprises an amino acid sequence selected from the group consisting of SEQ ID NOs: 2, 4, 6, 8, 10, 12, 14, or 16 or an amino acid sequence having at least 50%, 60%, 70%, 80%, 85%, 90%, or 95% sequence identity to an amino acid sequence of any of SEQ ID NOs: 2, 4, 6, 8, 10, 12, 14, or 16.

SEQ ID NO:1 is the variable heavy (VH) domain of the X19-A05 antibody as described in the following examples, and has the sequence:

EVQLLESGGGLVQPGGSLRLSCAASGFTFSGYWMHWVRQAPGKGLEWVS

YISPSGGGTHYADSVKGRFTISRDNSKNTLYLQMNSLRAEDTAVYYCAR

VRFRSVCSNAVCRPTAYDAFDI WGQGTMVTVSS, and includes the complementarity determining regions (CDRs):

```
                                              (SEQ ID NO: 17)
        VH CDR1: GYWM;

(SEQ ID NO: 18)
        VH CDR2: YISPSGGGTHYADSVKG;

(SEQ ID NO: 19)
        VH CDR3: VRFRSVCSNAVCRPTAYDAFDI;
```

SEQ ID NO:2 is the variable light (VL) domain of the X19-A05 antibody and has the sequence:

DIVMTQSPDSLAVSLGERATINCKSSQSVFYQSNKKNYLAWYQQKPGQPP

KLLIYWASTRESGVPDRFSGSGSGTDFTLTISSLQAEDVAVYYCQQYFNA

PRTFGQGTKVEIK, and includes the complementarity determining regions (CDRs):

```
                                              (SEQ ID NO: 23)
        VL CDR4: KSSQSVFYQSNKKNYLA;

(SEQ ID NO: 25)
        VL CDR5: WASTRES;

(SEQ ID NO: 26)
        VL CDR6: QQYFNAPRT,
```

SEQ ID NO:3 is the variable heavy (VH) domain of the M99-B05 antibody as described in the following examples, and has the sequence:

EVQLLESGGGLVQPGGSLRLSCAASGFTSGYWMHWVRQAPGKGLEWVSYI

SPSGGGTHYADSVKGRFTISRDNSKNTLYLQMNSLRAEDTAVYYCARVRF

RSVCSNGVCRPTAYDAFDIWGQGTAVTVSS, and includes the complementarity determining regions (CDRs):

```
                                  (SEQ ID NO: 17)
VH CDR1:         GYWM;

(SEQ ID NO: 18)
VH CDR2:         YISPSGGGTHYADSVKG;

(SEQ ID NO: 20)
VH CDR3:         VRFRSVCSNGVCRPTAYDAFDI,
```

SEQ ID NO:4 is the variable light (VL) domain of the M99-B05 antibody and has the sequence:

QDIQMTQSPDSLAVSLGERATINCKSSQSVFYNSNKKNYLAWYQQKAGQP

PKLLIHWASTRESGVPDRFSGSGSGTDFTLTISNLQAEDVALYYCQQYFN

APRTFGQGTKVEIK, and includes the complementarity determining regions (CDRs):

```
                                  (SEQ ID NO: 24)
VL CDR4:         KSSQSVFYNSNKKNYLA;

(SEQ ID NO: 25)
VL CDR5:         WASTRES;

(SEQ ID NO: 26)
VL CDR6:         QQYFNAPRT,
```

SEQ ID NO:5 is the variable heavy (VH) domain of the X19-A01 antibody as described in the following examples, and has the sequence:

EVQLLESGGGLVQPGGSLRLSCAASGFTSGYWMHWVRQAPGKGLEWVSYI

SPSGGGTHYADSVKGRFTISRDNSKNTLYLQMNSLRAEDTAVYYCARVRF

RSVCSNGVCRPTAYDAFDIWGQGTAVTVSS, and includes the complementarity determining regions (CDRs):

```
                                  (SEQ ID NO: 17)
VH CDR1:         GYWM;

(SEQ ID NO: 18)
VH CDR2:         YISPSGGGTHYADSVKG;

(SEQ ID NO: 20)
VH CDR3:         VRFRSVCSNGVCRPTAYDAFDI,
```

SEQ ID NO:6 is the variable light (VL) domain of the X19-A01 antibody and has the sequence:

DIQMTQSPDSLAVSLGERATINCKSSQSVFYNSNKKNYLAWYQQKAGQPP

KLLIHWASTRESGVPDRFSGSGSGTDFTLTISNLQAEDVALYYCQQYFNA

PRTFGQGTKVEIK, and includes the complementarity determining regions (CDRs):

```
                                  (SEQ ID NO: 24)
VL CDR4:         KSSQSVFYNSNKKNYLA;

(SEQ ID NO: 25)
VL CDR5:         WASTRES;

(SEQ ID NO: 26)
VL CDR6:         QQYFNAPRT,
```

SEQ ID NO:7 is the variable heavy (VH) domain of the X19-A03 antibody as described in the following examples, and has the sequence:

EVQLLESGGGLVQPGGSLRLSCAASGFTSGYWMHWVRQAPGKGLEWVSYI

SPSGGGTHYADSVKGRFTISRDNSKNTLYLQMNSLRAEDTAVYYCARVRF

RSVCSNAVCRPTAYDAFDIWGQGTMVTVSS, and includes the complementarity determining regions (CDRs):

```
                                  (SEQ ID NO: 17)
VH CDR1:         GYWM;

(SEQ ID NO: 18)
VH CDR2:         YISPSGGGTHYADSVKG;

(SEQ ID NO: 19)
VH CDR3:         VRFRSVCSNAVCRPTAYDAFDI,
```

SEQ ID NO:8 is the variable light (VL) domain of the X19-A03 antibody and has the sequence:

DIVMTQSPDSLAVSLGERATINCKSSQSVFYQSNKKNYLAWYQQKPGQPP

KLLIYWASTRESGVPDRFSGSGSGTDFTLTISSLQAEDVAVYYCQQYFNA

PRTFGQGTKVEIK, and includes the complementarity determining regions (CDRs):

```
                                  (SEQ ID NO: 23)
VL CDR4:         KSSQSVFYQSNKKNYLA;

(SEQ ID NO: 25)
VL CDR5:         WASTRES;

(SEQ ID NO: 26)
VL CDR6:         QQYFNAPRT,
```

SEQ ID NO:9 is the variable heavy (VH) domain of the X19-A07 antibody as described in the following examples, and has the sequence:

EVQLLESGGGLVQPGGSLRLSCAASGFTSGYWMHWVRQAPGKGLEWVSYI

SPSGGGTHYADSVKGRFTISRDNSKNTLYLQMNSLRAEDTAVYYCARVRF

RSVCSNGVCRPTAYDAFDIWGQGTMVTVSS, and includes the complementarity determining regions (CDRs):

```
                                  (SEQ ID NO: 17)
VH CDR1:         GYWM;

(SEQ ID NO: 18)
VH CDR2:         YISPSGGGTHYADSVKG;

(SEQ ID NO: 20)
VH CDR3:         VRFRSVCSNGVCRPTAYDAFDI,
```

SEQ ID NO:10 is the variable light (VL) domain of the X19-A07 antibody and has the sequence:

DIVMTQSPDSLAVSLGERATINCKSSQSVFYNSNKKNYLAWYQQKPGQPP

KLLIYWASTRESGVPDRFSGSGSGTDFTLTISSLQAEDVAVYYCQQYFNA

PRTFGQGTKVEIK, and includes the complementarity determining regions (CDRs):

```
                                              (SEQ ID NO: 24)
          VL CDR4: KSSQSVFYNSNKKNYLA;
                                              (SEQ ID NO: 25)
          VL CDR5: WASTRES;
                                              (SEQ ID NO: 26)
          VL CDR6: QQYFNAPRT,
```

SEQ ID NO:11 is the variable heavy (VH) domain of the X19-A09 antibody as described in the following examples, and has the sequence:

EVQLLESGGGLVQPGGSLRLSCAASGFTFSGYWMHWVRQAPGKGLEWVS

YISPSGGGTHYADSVKGRFTISRDNSKNTLYLQMNSLRAEDTAVYYCAR

VRFRSVCSNGVCRPTAYDAFDIWGQGTMVTVSS, and includes the complementarity determining regions (CDRs):

```
                                              (SEQ ID NO: 17)
          VH CDR1: GYWM;
                                              (SEQ ID NO: 18)
          VH CDR2: YISPSGGGTHYADSVKG;
                                              (SEQ ID NO: 20)
          VH CDR3: VRFRSVCSNGVCRPTAYDAFDI,
```

SEQ ID NO:12 is the variable light (VL) domain of the X19-A09 antibody and has the sequence:

DIVMTQSPDSLAVSLGERATINCKSSQSVFYNSNKKNYLAWYQQKPGQPP

KLLIYWASTRESGVPDRFSGSGSGTDFTLTISSLQAEDVAVYYCQQYFNA

PRTFGQGTKVEIK, and includes the complementarity determining regions (CDRs):

```
                                              (SEQ ID NO: 24)
          VL CDR4: KSSQSVFYNSNKKNYLA;
                                              (SEQ ID NO: 25)
          VL CDR5: WASTRES;
                                              (SEQ ID NO: 26)
          VL CDR6: QQYFNAPRT,
```

SEQ ID NO:13 is the variable heavy (VH) domain of the X19-A11 antibody as described in the following examples, and has the sequence:

EVQLLESGGGLVQPGGSLRLSCAASGFTSGYWMHWVRQAPGKGLEWVSYI

SPSGGGTHYADSVKGRFTISRDNSKNTLYLQMNSLRAEDTAVYYCARVRF

RSVSSNGVSRPTAYDAFDIWGQGTAVTVSS, and includes the complementarity determining regions (CDRs):

```
                                              (SEQ ID NO: 17)
          VH CDR1: GYWM;
                                              (SEQ ID NO: 18)
          VH CDR2: YISPSGGGTHYADSVKG;
                                              (SEQ ID NO: 21)
          VH CDR3: VRFRSVSSNGVSRPTAYDAFDI,
```

SEQ ID NO:14 is the variable light (VL) domain of the X19-A11 antibody and has the sequence:

DIQMTQSPDSLAVSLGERATINCKSSQSVFYNSNKKNYLAWYQQKAGQPP

KLLIHWASTRESGVPDRFSGSGSGTDFTLTISNLQAEDVALYYCQQYFNA

PRTFGQGTKVEIK, and includes the complementarity determining regions (CDRs):

```
                                              (SEQ ID NO: 24)
          VL CDR4: KSSQSVFYNSNKKNYLA;
                                              (SEQ ID NO: 25)
          VL CDR5: WASTRES;
                                              (SEQ ID NO: 26)
          VL CDR6: QQYFNAPRT,
```

SEQ ID NO:15 is the variable heavy (VH) domain of the X19-001 antibody as described in the following examples, and has the sequence:

EVQLLESGGGLVQPGGSLRLSCAASGFTSGYWMHWVRQAPGKGLEWVSYI

SPSGGGTHYADSVKGRFTISRDNSKNTLYLQMNSLRAEDTAVYYCARVRF

RSVSSNAVSRPTAYDAFDIWGQGTMVTVSS, and includes the complementarity determining regions (CDRs):

```
                                              (SEQ ID NO: 17)
          VH CDR1: GYWM;
                                              (SEQ ID NO: 18)
          VH CDR2: YISPSGGGTHYADSVKG;
                                              (SEQ ID NO: 22)
          VH CDR3: VRFRSVSSNAVSRPTAYDAFDI,
```

SEQ ID NO:16 is the variable light (VL) domain of the X19-001 antibody and has the sequence:

DIVMTQSPDSLAVSLGERATINCKSSQSVFYQSNKKNYLAWYQQKPGQPP

KLLIYWASTRESGVPDRFSGSGSGTDFTLTISSLQAEDVAVYYCQQYFNA

PRTFGQGTKVEIK, and includes the complementarity determining regions (CDRs):

```
                                              (SEQ ID NO: 23)
          VL CDR4: KSSQSVFYQSNKKNYLA;
```

-continued

VL CDR5: WASTRES; (SEQ ID NO: 25)

VL CDR6: QQYFNAPRT. (SEQ ID NO: 26)

A summary of the SEQ ID NOS, as defined above, is shown as follows:

|        | VH              | VL              | CDR1             | CDR2             | CDR3             | CDR4             | CDR5             | CDR6             |
|--------|-----------------|-----------------|------------------|------------------|------------------|------------------|------------------|------------------|
| X19-A05 | SEQ ID NO: 1   | SEQ ID NO: 2   | SEQ ID NO: 17   | SEQ ID NO: 18   | SEQ ID NO: 19   | SEQ ID NO: 23   | SEQ ID NO: 25   | SEQ ID NO: 26   |
| M99-B05 | SEQ ID NO: 3   | SEQ ID NO: 4   | SEQ ID NO: 17   | SEQ ID NO: 18   | SEQ ID NO: 20   | SEQ ID NO: 24   | SEQ ID NO: 25   | SEQ ID NO: 26   |
| X19-A01 | SEQ ID NO: 5   | SEQ ID NO: 6   | SEQ ID NO: 17   | SEQ ID NO: 18   | SEQ ID NO: 20   | SEQ ID NO: 24   | SEQ ID NO: 25   | SEQ ID NO: 26   |
| X19-A03 | SEQ ID NO: 7   | SEQ ID NO: 8   | SEQ ID NO: 17   | SEQ ID NO: 18   | SEQ ID NO: 19   | SEQ ID NO: 23   | SEQ ID NO: 25   | SEQ ID NO: 26   |
| X19-A07 | SEQ ID NO: 9   | SEQ ID NO: 10  | SEQ ID NO: 17   | SEQ ID NO: 18   | SEQ ID NO: 20   | SEQ ID NO: 24   | SEQ ID NO: 25   | SEQ ID NO: 26   |
| X19-A09 | SEQ ID NO: 11  | SEQ ID NO: 12  | SEQ ID NO: 17   | SEQ ID NO: 18   | SEQ ID NO: 20   | SEQ ID NO: 24   | SEQ ID NO: 25   | SEQ ID NO: 26   |
| X19-A11 | SEQ ID NO: 13  | SEQ ID NO: 14  | SEQ ID NO: 17   | SEQ ID NO: 18   | SEQ ID NO: 21   | SEQ ID NO: 24   | SEQ ID NO: 25   | SEQ ID NO: 26   |
| X19-C01 | SEQ ID NO: 15  | SEQ ID NO: 16  | SEQ ID NO: 17   | SEQ ID NO: 18   | SEQ ID NO: 22   | SEQ ID NO: 23   | SEQ ID NO: 25   | SEQ ID NO: 26   |

In a further embodiment of the first aspect of the invention, the antibody or antibody fragment is based on the VH and/or VL domains of the X19-A05 antibody, and so— the VH domain (i) comprises an amino acid sequence having at least 80%, 85%, 90%, 95% or 100% sequence identity SEQ ID NO:1 and/or (ii) comprises a CDR1 sequence comprising an amino acid sequence having at least 25%, 50%, 75% or 100% sequence identity to the sequence of SEQ ID NO: 17, a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18, and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 19; and/or the VL domain (iii) comprises an amino acid sequence having at least 80%, 85%, 90%, 95% or 100% sequence identity SEQ ID NO: 2 and/or (iv) comprises a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 23, a CDR5 sequence comprising an amino acid sequence having at least 14%, 28%, 42%, 57%, 71%, 85% or 100% sequence identity to the sequence of SEQ ID NO: 25 and a CDR6 sequence comprising an amino acid sequence having at least 11%, 22%, 33%, 44%, 55%, 66%, 77%, 88% or 100% sequence identity to the sequence of SEQ ID NO: 26. It may be preferred that the VH domain comprises the sequence of SEQ ID NO:1 and the VL domain comprises the sequence of SEQ ID NO: 2.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include:

(SEQ ID NO: 27)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK;
and (SEQ ID NO: 28)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG.

SEQ ID NO:27 is the CH region of M99-B05 and has the sequence of a CH region of Human IgG1 (UniProtKB/Swiss-Prot: P01857.1). SEQ ID NO: 28 is the CH region of X19-A05. SEQ ID NO: 28 differs from SEQ ID NO: 27 by the removal of the terminal K (Lys) in the CH region of SEQ ID NO: 28, which reduces or avoids the potential for peptidase degradation.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes:

```
                                            (SEQ ID NO: 29)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

SEQ ID NO:29 is the CL region of both of M99-B05 and X19-A05, and possesses the sequence of the CL region of Human kappa (UniProtKB/Swiss-Prot: P01834.1).

According to this embodiment, it may be preferred that the VH domain comprises the sequence of SEQ ID NO:1, linked to the CH region of SEQ ID NO: 28 and the VL domain comprises the sequence of SEQ ID NO: 2 linked to the CL region of SEQ ID NO: 29.

In another embodiment of the first aspect of the invention, the antibody or antibody fragment is based on the VH and/or VL domains of the M99-B05 antibody, and so— the VH domain (i) comprises an amino acid sequence having at least 80%, 85%, 90%, 95% or 100% sequence identity SEQ ID NO:3 and/or (ii) comprises a CDR1 sequence comprising an amino acid sequence having at least 25%, 50%, 75% or 100% sequence identity to the sequence of SEQ ID NO: 17, a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18, and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 20; and/or the VL domain (iii) comprises an amino acid sequence having at least 80%, 85%, 90%, 95% or 100% sequence identity SEQ ID NO: 4 and/or (iv) comprises a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 24, a CDR5 sequence comprising an amino acid sequence having at least 14%, 28%, 42%, 57%, 71%, 85% or 100% sequence identity to the sequence of SEQ ID NO: 25 and a CDR6 sequence comprising an amino acid sequence having at least 11%, 22%, 33%, 44%, 55%, 66%, 77%, 88% or 100% sequence identity to the sequence of SEQ ID NO: 26. It may be preferred that the VH domain comprises the sequence of SEQ ID NO:3 and the VL domain comprises the sequence of SEQ ID NO: 4.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include SEQ ID NO: 27 and SEQ ID NO: 28.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes SEQ ID NO: 29.

According to this embodiment, it may be preferred that the VH domain comprises the sequence of SEQ ID NO:3, linked to the CH region of SEQ ID NO: 27 or 28 and the VL domain comprises the sequence of SEQ ID NO: 4 linked to the CL region of SEQ ID NO: 29.

In another embodiment of the first aspect of the invention, the antibody or antibody fragment is based on the VH and/or VL domains of the X19-A01 antibody, and so— the VH domain (i) comprises an amino acid sequence having at least 80%, 85%, 90%, 95% or 100% sequence identity SEQ ID NO:5 and/or (ii) comprises a CDR1 sequence comprising an amino acid sequence having at least 25%, 50%, 75% or 100% sequence identity to the sequence of SEQ ID NO: 17, a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18, and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 20; and/or the VL domain (i) comprises an amino acid sequence having at least 80%, 85%, 90%, 95% or 100% sequence identity SEQ ID NO: 6 and/or (iv) comprises a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 24, a CDR5 sequence comprising an amino acid sequence having at least 14%, 28%, 42%, 57%, 71%, 85% or 100% sequence identity to the sequence of SEQ ID NO: 25 and a CDR6 sequence comprising an amino acid sequence having at least 11%, 22%, 33%, 44%, 55%, 66%, 77%, 88% or 100% sequence identity to the sequence of SEQ ID NO: 26. It may be preferred that the VH domain comprises the sequence of SEQ ID NO:5 and the VL domain comprises the sequence of SEQ ID NO: 6.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include SEQ ID NO: 27 and SEQ ID NO: 28.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes SEQ ID NO: 29.

According to this embodiment, it may be preferred that the VH domain comprises the sequence of SEQ ID NO:5, linked to the CH region of SEQ ID NO: 27 or 28 and the VL domain comprises the sequence of SEQ ID NO: 6 linked to the CL region of SEQ ID NO: 29.

In another embodiment of the first aspect of the invention, the antibody or antibody fragment is based on the VH and/or VL domains of the X19-A03 antibody, and so—
- the VH domain (i) comprises an amino acid sequence having at least 80%, 85%, 90%, 95% or 100% sequence identity SEQ ID NO:7 and/or (ii) comprises a CDR1 sequence comprising an amino acid sequence having at least 25%, 50%, 75% or 100% sequence identity to the sequence of SEQ ID NO: 17, a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18, and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 19; and/or
- the VL domain (iii) comprises an amino acid sequence having at least 80%, 85%, 90%, 95% or 100% sequence identity SEQ ID NO: 8 and/or (iv) comprises a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 23, a CDR5 sequence comprising an amino acid sequence having at least 14%, 28%, 42%, 57%, 71%, 85% or 100% sequence identity to the sequence of SEQ ID NO: 25 and a CDR6 sequence comprising an amino acid sequence having at least 11%, 22%, 33%, 44%, 55%, 66%, 77%, 88% or 100% sequence identity to the sequence of SEQ ID NO: 26. It may be preferred that the VH domain comprises the sequence of SEQ ID NO:7 and the VL domain comprises the sequence of SEQ ID NO: 8.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include SEQ ID NO: 27 and SEQ ID NO: 28.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes SEQ ID NO: 29.

According to this embodiment, it may be preferred that the VH domain comprises the sequence of SEQ ID NO:7, linked to the CH region of SEQ ID NO: 27 or 28 and the VL domain comprises the sequence of SEQ ID NO: 8 linked to the CL region of SEQ ID NO: 29.

In another embodiment of the first aspect of the invention, the antibody or antibody fragment is based on the VH and/or VL domains of the X19-A07 antibody, and so—
- the VH domain (i) comprises an amino acid sequence having at least 80%, 85%, 90%, 95% or 100% sequence identity SEQ ID NO:9 and/or (ii) comprises a CDR1 sequence comprising an amino acid sequence having at least 25%, 50%, 75% or 100% sequence identity to the sequence of SEQ ID NO: 17, a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18, and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 20; and/or
- the VL domain (iii) comprises an amino acid sequence having at least 80%, 85%, 90%, 95% or 100% sequence identity SEQ ID NO: 10 and/or (iv) comprises a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 24, a CDR5 sequence comprising an amino acid sequence having at least 14%, 28%, 42%, 57%, 71%, 85% or 100% sequence identity to the sequence of SEQ ID NO: 25 and a CDR6 sequence comprising an amino acid sequence having at least 11%, 22%, 33%, 44%, 55%, 66%, 77%, 88% or 100% sequence identity to the sequence of SEQ ID NO: 26. It may be preferred that the VH domain comprises the sequence of SEQ ID NO:9 and the VL domain comprises the sequence of SEQ ID NO: 10.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include SEQ ID NO: 27 and SEQ ID NO: 28.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes SEQ ID NO: 29

According to this embodiment, it may be preferred that the VH domain comprises the sequence of SEQ ID NO:9, linked to the CH region of SEQ ID NO: 27 or 28 and the VL domain comprises the sequence of SEQ ID NO: 10 linked to the CL region of SEQ ID NO: 29.

In another embodiment of the first aspect of the invention, the antibody or antibody fragment is based on the VH and/or VL domains of the X19-A09 antibody, and so— the VH domain (i) comprises an amino acid sequence having at least 80%, 85%, 90%, 95% or 100% sequence identity SEQ ID NO:11 and/or (ii) comprises a CDR1 sequence comprising an amino acid sequence having at least 25%, 50%, 75% or 100% sequence identity to the sequence of SEQ ID NO: 17, a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18, and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 20; and/or the VL domain (iii) comprises an amino acid sequence having at least 80%, 85%, 90%, 95% or 100% sequence identity SEQ ID NO: 12 and/or (iv) comprises a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 24, a CDR5 sequence comprising an amino acid sequence having at least 14%, 28%, 42%, 57%, 71%, 85% or 100% sequence identity to the sequence of SEQ ID NO: 25 and a CDR6 sequence comprising an amino acid sequence having at least 11%, 22%, 33%, 44%, 55%, 66%, 77%, 88% or 100% sequence identity to the sequence of SEQ ID NO: 26. It may be preferred that the VH domain comprises the sequence of SEQ ID NO:11 and the VL domain comprises the sequence of SEQ ID NO: 12.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include SEQ ID NO: 27 and SEQ ID NO: 28.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes SEQ ID NO: 29.

According to this embodiment, it may be preferred that the VH domain comprises the sequence of SEQ ID NO:11, linked to the CH region of SEQ ID NO: 27 or 28 and the VL domain comprises the sequence of SEQ ID NO: 12 linked to the CL region of SEQ ID NO: 29.

In another embodiment of the first aspect of the invention, the antibody or antibody fragment is based on the VH and/or VL domains of the X19-A11 antibody, and so— the VH domain (i) comprises an amino acid sequence having at least 80%, 85%, 90%, 95% or 100% sequence identity SEQ ID NO:13 and/or (ii) comprises a CDR1 sequence comprising an amino acid sequence having at least 25%, 50%, 75% or 100% sequence identity to the sequence of SEQ ID NO: 17, a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18, and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 21; and/or the VL domain (i) comprises an amino acid sequence having at least 80%, 85%, 90%, 95% or 100% sequence identity SEQ ID NO: 14 and/or (iv) comprises a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 24, a CDR5 sequence comprising an amino acid sequence having at least 14%, 28%, 42%, 57%, 71%, 85% or 100% sequence identity to the sequence of SEQ ID NO: 25 and a CDR6 sequence comprising an amino acid sequence having at least 11%, 22%, 33%, 44%, 55%, 66%, 77%, 88% or 100% sequence identity to the sequence of SEQ ID NO: 26. It may be preferred that the VH domain comprises the sequence of SEQ ID NO:13 and the VL domain comprises the sequence of SEQ ID NO: 14.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include SEQ ID NO: 27 and SEQ ID NO: 28.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes SEQ ID NO: 29.

According to this embodiment, it may be preferred that the VH domain comprises the sequence of SEQ ID NO:13, linked to the CH region of SEQ ID NO: 27 or 28 and the VL domain comprises the sequence of SEQ ID NO: 14 linked to the CL region of SEQ ID NO: 29.

In another embodiment of the first aspect of the invention, the antibody or antibody fragment is based on the VH and/or VL domains of the X19-001 antibody, and so— the VH domain (i) comprises an amino acid sequence having at least 80%, 85%, 90%, 95% or 100% sequence identity SEQ ID NO:15 and/or (ii) comprises a CDR1 sequence comprising an amino acid sequence having at least 25%, 50%, 75% or 100% sequence identity to the sequence of SEQ ID NO: 17, a CDR2 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 18, and a CDR3 sequence comprising an amino acid sequence having at least 4%, 9%, 13%, 18%, 22%, 27%, 31%, 36%, 40%, 45%, 50%, 54%, 59%, 63%, 68%, 72%, 77%, 81%, 86%, 90%, 95% or 100% sequence identity to the sequence of SEQ ID NO: 22; and/or the VL domain (iii) comprises an amino acid sequence having at least 80%, 85%, 90%, 95% or 100% sequence identity SEQ ID NO: 16 and/or (iv) comprises a CDR4 sequence comprising an amino acid sequence having at least 5%, 11%, 17%, 23%, 29%, 35%, 47%, 52%, 58%, 64%, 70%, 76%, 82%, 94% or 100% sequence identity to the sequence of SEQ ID NO: 23, a CDR5 sequence comprising an amino acid sequence having at least 14%, 28%, 42%, 57%, 71%, 85% or 100% sequence identity to the sequence of SEQ ID NO: 25 and a CDR6 sequence comprising an amino acid sequence having at least 11%, 22%, 33%, 44%, 55%, 66%, 77%, 88% or 100% sequence identity to the sequence of SEQ ID NO: 26. It may be preferred that the VH domain comprises the sequence of SEQ ID NO:15 and the VL domain comprises the sequence of SEQ ID NO: 16.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include SEQ ID NO: 27 and SEQ ID NO: 28.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes SEQ ID NO: 29

According to this embodiment, it may be preferred that the VH domain comprises the sequence of SEQ ID NO:15, linked to the CH region of SEQ ID NO: 27 or 28 and the VL domain comprises the sequence of SEQ ID NO: 16 linked to the CL region of SEQ ID NO: 29.

In the various foregoing embodiments, the discussion of CH regions and fragments thereof is also intended to include the option of using a variant of either. The variant comprises a sequence having less than 100% sequence identity to the stated CH region or fragment thereof, such as greater than 50%, 60%, 70%, 80%, 85%, 90%, 95%, 96%, 97%, 98%, or 99% sequence identity. Accordingly, variants of a CH region or a fragment thereof may posses one or more (such as 2, 3, 4, 5, 6, 7, 8, 9, 10, 15, 20, 25, 30, 40, 50, 60, 70 80, 90, 100, 110, 120, 130, 140, 150 160 or more) sequence variations compared to the stated CH region or fragment thereof. Variations in sequence may be due to one or more amino acid additions, one or more amino acid deletions and/or one or more amino acid substitutions compared to the stated CH region or fragment thereof. Where there is more than one variation, then the variations may be in consecutive or non-consecutive positions.

Likewise, in the various foregoing embodiments, the discussion of CL regions and fragments thereof is also intended to include the option of using a variant of either. The variant comprises a sequence having less than 100% sequence identity to the stated CL region or fragment thereof, such as greater than 50%, 60%, 70%, 80%, 85%, 90%, 95%, 96%, 97%, 98%, or 99% sequence identity. Accordingly, variants of a CL region or a fragment thereof may posses one or more (such as 2, 3, 4, 5, 6, 7, 8, 9, 10, 15, 20, 25, 30, 40, 50, 60 or more) sequence variations compared to the stated CL region or fragment thereof. Variations in sequence may be due to one or more amino acid additions, one or more amino acid deletions and/or one or more amino acid substitutions compared to the stated CL region or fragment thereof. Where there is more than one variation, then the variations may be in consecutive or non-consecutive positions.

In the antibody or antibody fragment according to the foregoing embodiments, it may be preferred that the VH domain, the VL domain, or preferably both of the VH and VL domains, comprise an amino acid sequence having 100% sequence identity to the, or in the case of stated SEQ ID NOs that correspond to individual CDR sequences then one or more (such as, two or three) of each, stated SEQ ID NO.

Alternatively, the VH domain, the VL domain, or both of the VH and VL domains, may comprise an amino acid sequence having less than 100% sequence identity to the, or in the case of stated SEQ ID NOs that correspond to individual CDR sequences then one or more (such as, two or three) of each, stated SEQ ID NO.

In accordance with the first aspect of the present invention, a sequence comprising an amino acid sequence having less than 100% to the stated SEQ ID NO may be a sequence possessing one or more (such as 2, 3, 4, 5, 6, 7, 8, 9, 10 or more) sequence variations compared to the stated SEQ ID NO. Variations in sequence may be due to one or more (such as 2, 3, 4, 5, 6, 7, 8, 9, 10 or more) amino acid additions, one or more (such as 2, 3, 4, 5, 6, 7, 8, 9, 10 or more) amino acid deletions and/or one or more (such as 2, 3, 4, 5, 6, 7, 8, 9, 10 or more) amino acid substitutions compared to the stated SEQ ID NO. Where there is more than one variation, then the variations may be in consecutive or non-consecutive positions.

The one or more variations in sequence in a variant antigen binding region that has less than 100%, but at least 80%, 85%, 90%, 95%, sequence identity to a stated SEQ ID NO selected from SEQ ID NOs: 1 to 16 may be present in, or exclusively in, the amino acid sequence that form one or more of the framework regions. Framework regions comprise the amino acid regions that do not form the CDRs as defined herein.

Additionally or alternatively, one or more variations in sequence in an antigen binding region that has less than 100%, but at least 80%, 85%, 90%, 95%, sequence identity to a stated SEQ ID NO selected from SEQ ID NOs: 1 to 16 may be present in, or exclusively in, the amino acid sequence that form one or more of the complementarity determining regions (CDRs). The CDRs in SEQ ID NOs: 1-16 are as defined above and are also shown in Tables 2 and 3 below.

In all embodiments of the first aspect of the invention, in general higher levels of sequence modifications may be tolerated in the framework regions than in the CDRs without substantially altering the binding characteristics and/or in vivo efficacy of the antibody or antibody fragment.

Thus, for example, in a further embodiment, a, the, or each, CDR in an antibody or antibody fragment according to the first aspect of the present invention may comprise up to 1, 2, 3, 4, 5, 6, 7, 8, 9 or 10 amino acid substitutions, insertions and/or deletions compared to the 'parent' CDR sequence defined one of SEQ ID NOs 17 to 26 and preferably not more than 5, 4, 3, 2 or 1 amino acid substitutions, insertions and/or deletions; it may be preferred that the number of amino acid substitutions, insertions and/or deletions implemented in the CDR sequence to not reduce the level of sequence identity to less than 50%, 60%, 70%, 75%, 80%, 85%, 90%, 95% compared to the corresponding defined SEQ ID NO.

Additionally, and/or alternatively, a, the, or each, framework region in an antibody or antibody fragment according to the first aspect of the present invention may comprise up to 1, 2, 3, 4, 5, 6, 7, 8, 9, 10, 11, 12, 13, 14, 15, 16, 17, 18, 19, 20, or more amino acid substitutions, insertions and/or deletions compared to the corresponding framework sequence present in any of the VH or VL sequences defined SEQ ID NOs 1 to 16, and optionally not more than 10, 9, 8, 7, 6, 5, 4, 3, 2 or 1 amino acid substitutions, insertions and/or deletions; it may be preferred that the number of amino acid substitutions, insertions and/or deletions implemented in any framework region to not reduce the level of sequence identity to less than 10%, 20%, 30%, 40% 50%, 60%, 70%, 75%, 80%, 85%, 90%, 95% compared to the corresponding defined SEQ ID NO.

Substitutions, whether in one or more of the framework or complementarity determining regions, may be conservative or non-conservative substitutions. By "conservative substitutions" is intended combinations such as Gly, Ala; Val, Ile, Leu; Asp, Glu; Asn, Gln; Ser, Thr; Lys, Arg; and Phe, Tyr.

Sequence variations may, for example, be introduced in order to render the sequence of the antigen binding region(s) closer to germline sequences, to improve the stability of the antibody or antibody fragment comprising the variant antigen binding region(s), to reduce the immunogenicity of the antibody or antibody fragment comprising the variant antigen binding region(s), and/or to avoid or reduce properties that could be disadvantageous in the manufacturing process. Non-limiting examples of suitable sequence variations are shown in the examples with reference to the variations introduced into the heavy and/or light chain sequences of M99-B05 in order to produce X19-A01, X19-A03, X19-A05, X19-A07, X19-A09, X19-A11, and/or X19-001.

Such variants may be made using the methods of protein engineering and site-directed mutagenesis as described below or alternative methods that are well known in the art.

Where the VH domain, the VL domain, or both of the VH and VL domains, of the antibody or antibody fragment of the first aspect of the present invention comprise(s) one or more amino acid sequences having less than 100% sequence identity to the, or one or more of each, stated SEQ ID NO, then in one embodiment the ability of the antibody or antibody fragment to bind to phosphorylcholine and/or a phosphorylcholine conjugate may, for example, be substantially equivalent to (that is, at least 80%, 85%, 90% or 95%), or greater than, the ability of a corresponding 'parent' antibody or antibody fragment, wherein the VH domain and the VL domain of the corresponding 'parent' antibody or antibody fragment each comprise an amino acid sequence having 100% sequence identity to the, or each, stated SEQ ID NO.

Thus, for example, where the antibody or antibody fragment is based on the X19-A05 antibody, and the VH domain comprises an amino acid sequence having less than 100%, but at least 80%, 85%, 90%, or 95% sequence identity SEQ ID NO:1; and/or the VL domain comprises an amino acid sequence having less than 100%, but at least 80%, 85%, 90%, or 95% sequence identity SEQ ID NO: 2, then the ability of the antibody or antibody fragment to bind to phosphorylcholine and/or a phosphorylcholine conjugate may, for example, be equivalent to the binding ability of a corresponding 'parent' antibody or antibody fragment having a VH domain that comprises the sequence of SEQ ID NO:1 and a VL domain that comprises the sequence of SEQ ID NO: 2. In this context, by "corresponding 'parent' antibody or antibody fragment" is meant that the only sequence difference between the "antibody or antibody fragment" in hand and the "corresponding 'parent' antibody or antibody fragment" is in one or both of the VH and/or VL domains. In one embodiment, the corresponding parent antibody is an antibody having the sequence of the VH, VL, CH and CL regions of X19-A05, that is, a VH domain of SEQ ID NO:1 linked to the CH region of SEQ ID NO: 28 and the VL domain of SEQ ID NO: 2 linked to the CL region of SEQ ID NO: 29.

The same applies, mutatis mutandis, to the other antibody or antibody fragment listed above wherein the VH and/or VL domains comprise(s) one or more amino acid sequences having less than 100% sequence identity to the, or one or more of each, stated SEQ ID No, and the "corresponding 'parent' antibody or antibody fragment" for the purposes of determining binding equivalence to phosphorylcholine and/or a phosphorylcholine conjugate differs only in the one or both of the sequences of the VH and/or VL domain and possess(es) the, or each, sequence comprising an amino acid sequence having 100% sequence identity to the, or each, stated SEQ ID No.

Accordingly, where the antibody or antibody fragment is based on the M99-B05 then, in one embodiment, the corresponding parent antibody is an antibody having the sequence of the VH, VL, CH and CL regions of M99-B05, that is, a VH domain of SEQ ID NO:3 linked to the CH region of SEQ ID NO: 27 and the VL domain of SEQ ID NO: 4 linked to the CL region of SEQ ID NO: 29.

In this regard, the ability of an antibody or antibody fragment to bind to phosphorylcholine and/or a phosphorylcholine conjugate may be determined by any suitable method, such as by Surface Plasmon Resonance (SPR) analysis, to measure the binding of the antibody or antibody fragment to phosphorylcholine immobilized (for example via an aminophenyl linker) to a solid surface such as the Biacore SPR biosensor.

In an additional embodiment, an antibody or antibody fragment according to the first aspect of the present invention competes with a 'comparator' antibody or antibody fragment for binding to PC or a PC conjugate as defined herein (e.g., as determined in an ELISA or SPR assay). In this context, a comparator antibody or antibody fragment may comprise the VH and VL domains, and optionally also the CH and CL domains, of X19-A05 (as defined by SEQ ID NOs: 1, 2, 28 and 29, respectively), M99-B05 (as defined by SEQ ID NOs: 3, 4, 27 and 29), X19-A01 (as defined by SEQ ID NOs: 5, 6, 27 and 29, respectively), X19-A03 (as defined by SEQ ID NOs: 7, 8, 27 and 29, respectively), X19-A07 (as defined by SEQ ID NOs: 9, 10, 27 and 29, respectively), X19-A09 (as defined by SEQ ID NOs: 11, 12, 27 and 29, respectively), X19-A11 (as defined by SEQ ID NOs: 13, 14, 27 and 29, respectively) or X19-001 (as defined by SEQ ID NOs: 15, 16, 27 and 29, respectively) and preferably differs from the antibody or antibody fragment being tested only by sequence variation in the VH and/or VL regions. By 'competes', we mean that inclusion of equimolar amounts of the antibody or antibody fragment according to the first aspect of the present invention and the 'comparator' antibody in an assay can reduce the detectable level of binding to PC or a PC conjugate of the comparator antibody by 10%, 20%, 30%, 40%, 50%, 60%, 70%, 80%, 90%, 95% or more, such as substantially 100%, in comparison to the detectable level of binding to PC or a PC conjugate of the 'comparator' antibody in the same assay in the absence of the antibody or antibody fragment according to the first aspect of the present invention.

As discussed in the examples below, M99-B05 binds aminophenyl phosphorylcholine with an apparent Kd of about 150 nM. In one embodiment, an antibody or antibody fragment according to the present invention will bind to immobilized aminophenyl phosphorylcholine with an apparent Kd of no greater than about 500 nM, about 400 nM, about 300 nM, about 250 nM, about 200 nM, about 190 nM, about 180 nM, about 170 nM, about 160 nM, about 155 nM, about 150 nM, or less when tested under conditions (such as the SPR conditions used in the examples) that provide for binding of an antibody or antibody fragment having the VH and VL domains of M99-B05 (as defined by SEQ ID NOS 3 and 4, respectively) to immobilized aminophenyl phosphorylcholine with an apparent Kd of about 150 nM. In this context, the term "about" is used to mean a value that is within ±20%, 15%, 10%, 5%, 4%, 3%, 2%, or 1% of the stated value.

As also discussed in the examples below, M99-B05 can block the release of MCP-1 from monocytes in response to stimulation with oxLDL with an $IC_{50}$ in the nM range. In another embodiment, an antibody or antibody fragment according to the present invention will block the release of MCP-1 from monocytes in response to stimulation with oxLDL with an $IC_{50}$ of less than about 10 nM, about 5 nM, about 4 nM, about 3 nM, about 2.8 nM, about 2.6 nM, about 2.4 nM, about 2 nM, about 1.8 nM, about 1.6 nM, about 1.4 nM, about 1.3 nM, about 1.2 nM, about 1.1 nM, about 1.0 nM, about 0.9 nM, about 0.8 nM, about 0.7 nM or less when tested under conditions (such as described in the example below) that provide for an $IC_{50}$ of an antibody or antibody fragment having the VH and VL domains of M99-B05 (as defined by SEQ ID NOS 3 and 4, respectively) in the 0.7-2.6 nM range. In this context, the term "about" is used to mean a value that is within ±20%, 15%, 10%, 5%, 4%, 3%, 2%, or 1% of the stated value.

The ability of an antibody or antibody fragment according to the present invention to bind to a phosphorylcholine conjugate may be determined by equivalent methods to those described above, replacing phosphorylcholine with the phosphorylcholine conjugate. Suitable phosphorylcholine conjugates include those discussed above, comprising a phosphorylcholine moiety linked to a carrier, optionally via a spacer, such as PC-BSA and PC-KLH conjugates. Preferably, where the ability of an antibody or antibody fragment to bind to the phosphorylcholine conjugate is determined, it is determined with respect to the ability of the antibody or antibody fragment to bind specifically to the phosphorylcholine moiety in the phosphorylcholine conjugate. This can be determined by art-known techniques such as by comparing the ability of the antibody or antibody fragment to bind to the phosphorylcholine conjugate and the corresponding molecule that does not contain a phosphorylcholine moiety.

In one embodiment, the antibody or antibody fragment of the present invention may be comprise the VH domain and the VL domain in a linear polypeptide sequence.

In another embodiment, the antibody or antibody fragment of the present invention may comprise the VH domain and the VL domain each in a separate polypeptide sequence. In this embodiment, it may be preferred that the separate polypeptide sequence are directly or indirectly bound together (such as by one or more disulphide bonds between the separate polypeptide sequence).

In another embodiment, the VH domain may be joined to a CH region, or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region, or a variant of the CH region or a fragment thereof, as described above. The join may be a direct fusion via a peptide bond, such that the VH domain and CH region are presented as a single polypeptide, or the join may be through a linker, such as a peptide or other linker, or via a direct chemical bond other than a peptide bond. There is no particular limitation on the CH region although in one embodiment it is a human CH region. The art contains many examples of human CH regions. Exemplary human CH regions for use in this context include SEQ ID NO: 27 and SEQ ID NO: 28. When using any CH regions, terminal amino acid modifications (including the deletion of, or masking by addition of another amino acid or other chemical moiety) may be introduced to reduce or avoid the potential for peptidase degradation.

In another embodiment, the VL domain may be joined to a CL region, or a fragment may comprise, for example, at least 10, 20, 30, 40, 50, 60, 70, 80, 90, 100 or more amino acids of a CL region, or a variant of the CL region or a fragment thereof, as described above. The join may be a direct fusion via a peptide bond, such that the VL domain and CL region are presented as a single polypeptide, or the join may be through a linker, such as a peptide or other linker, or via a direct chemical bond other than a peptide bond. There is no particular limitation on the CL region although in one embodiment it is a human CL region. The art contains many examples of human CL regions. An exemplary human CL region for use in this context includes SEQ ID NO: 29. Terminal amino acid modifications (including the deletion of, or masking by addition of another amino acid or other chemical moiety) may be introduced to reduce or avoid the potential for peptidase degradation of any CL region that is used.

In another embodiment, the antibody or antibody fragment of the present invention may comprise a VH domain joined to a CH region in one polypeptide sequence, and a VL domain joined to a CL region in another separate polypeptide sequence. In this embodiment, it may be preferred that the separate polypeptide sequence are directly or indirectly bound together (such as by one or more disulphide bonds between the separate polypeptide sequence).

In a further embodiment, the antibody or antibody fragment of the present invention may comprise—
  a first heavy chain comprising a first VH domain joined to a first CH region,
  a first light chain comprising a first VL domain joined to a first CL region;
  a second heavy chain comprising a second VH domain joined to a second CH region,
  a second light chain comprising a second VL domain joined to a second CL region; and
wherein optionally, the first light and first heavy chains are directly or indirectly bound together (such as by one or more disulphide bonds between the separate polypeptide sequence) and the second light and second heavy chains are directly or indirectly bound together (such as by one or more disulphide bonds between the separate polypeptide sequence), and further optionally, wherein the first and second heavy chains directly or indirectly bound together (such as by one or more disulphide bonds between the separate polypeptide sequence).

In a further embodiment, the antibody or antibody fragment of the present invention may be a monoclonal antibody, more preferably a human monoclonal antibody.

The antibody or antibody fragment of the present invention may be a humanized antibody or a chimeric antibody.

In one preferred embodiment, the antibody or antibody fragment of the present invention is an isolated antibody or antibody fragment.

In another embodiment, the antibody or antibody fragment of the present invention may comprise one or more of the amino acid sequences comprising the VH, VL, CDR1, CDR2, CDR3, CDR4, CDR5 and/or CDR6 sequences described above grafted onto a protein scaffolds of immunoglobulins using standard protein engineering techniques. The skilled person will appreciate that various protein scaffolds are available for use and commonly known in the art. The end result is preserved antigen-binding activity in a new framework.

For example, the scaffolds of immunoglobulins can be derived from IgA, IgE, IgG1, IgG2a, IgG2b, IgG3, IgM. The scaffolds can be derived from an immunoglobulin from any mammal, such as mice, rats, rabbits, goats, camels, llamas, primates. It may be preferred that the immunoglobulin scaffold is derived from human immunoglobulins.

The antibody fragments according to the first aspect of the present invention can be generated by standard molecular biology techniques or by cleavage of purified antibodies using enzymes (e.g. pepsin or papain) that generates these fragments. Such antibody fragments according to the invention are exemplified, but not limited to, single chain antibodies, Fv, scFv, Fab, F(ab')$_2$, Fab', Fd, dAb, CDR, or scFv-Fc fragments or nanobodies, and diabodies, or any fragment that may have been stabilized by e.g. PEGylation.

A second aspect of the present invention provides a pharmaceutical composition comprising an antibody or an antibody fragment according to the first aspect of the invention and a pharmaceutically acceptable carrier or excipient. Optionally, the only antibodies or antibody fragments present in the composition are those of the first aspect of the present invention. More preferably, there may be a single type of antibody or antibody fragment present in the composition, for example wherein type is determined with respect to amino acid sequence, molecular weight and/or binding specificity to phosphorylcholine. In this regard, the skilled person will appreciate that there may be some low levels of variation in the sequences of antibodies or antibody fragments in any population due, for example, to N-terminal variation and/or partial degradation; accordingly, in this context, a composition can be said to contain a single type of antibody or antibody fragment if, for example, at least about 80%, about 90%, about 95%, about 96%, about 97%, about 98%, about 99% or substantially 100% by weight of the detectable level of antibodies or antibody fragments in the composition are of a single type as determined with respect to amino acid sequence, molecular weight and/or binding specificity to phosphorylcholine.

A third aspect of the present invention provides an antibody or antibody fragment according to the first aspect of the present invention, or a pharmaceutical composition according to the second aspect of the present invention for use in medicine, such as for use in a method of therapy, surgery or diagnosis that is performed on the human or animal body or on an ex vivo sample therefrom.

For example, the third aspect of the present invention provides an antibody or antibody fragment according to the first aspect of the present invention, or a pharmaceutical composition according to the second aspect of the present invention, for use in the prevention, prophylaxis and/or treatment of mammals, including humans, against atherosclerosis, an atherosclerotic related disease or cardiovascular disease.

In other words, the third aspect of the present invention provides for the use of an antibody or antibody fragment according to the first aspect of the present invention, or a pharmaceutical composition according to the second aspect of the present invention, in the manufacture of a medicament for the prevention, prophylaxis and/or treatment of mammals, including humans, against atherosclerosis, an atherosclerotic related disease or cardiovascular disease.

Also provided is a method for prevention, prophylaxis and/or treatment of a mammal, including a human, against atherosclerosis, an atherosclerotic related disease, or cardiovascular disease, the method comprising the step of administering to the mammal an antibody or antibody fragment according to the first aspect of the invention, or a pharmaceutical composition according to the second aspect of the invention.

The third aspect of the present invention also provides an antibody or antibody fragment according to the first aspect of the present invention, or a pharmaceutical composition according to the second aspect of the present invention, for use in the prophylaxis, prevention and/or treatment of Alzheimer's disease.

In other words, the third aspect of the present invention provides for the use of an antibody or antibody fragment according to the first aspect of the present invention, or a pharmaceutical composition according to the second aspect of the present invention, in the manufacture of a medicament for the prophylaxis, prevention and/or treatment of Alzheimer's disease.

Also provided is a method for immunization and prophylaxis, prevention and/or treatment of a subject against Alzheimer's disease, the method comprising the step of administering to the subject an antibody or antibody fragment according to the first aspect of the invention, or a pharmaceutical composition according to the second aspect of the invention.

The third aspect of the present invention also provides an antibody or antibody fragment according to the first aspect of the present invention, or a pharmaceutical composition according to the second aspect of the present invention, for use in the immunization or prophylaxis against, or the prevention or treatment of, metabolic disease in mammals, including humans.

In other words, the third aspect of the present invention provides for the use of an antibody or antibody fragment according to the first aspect of the present invention, or a pharmaceutical composition according to the second aspect of the present invention, in the manufacture of a medicament for the prophylaxis, prevention or treatment of, metabolic disease in mammals, including humans.

Also provided is a method for the immunization or prophylaxis against, or the treatment of, metabolic diseases in a mammal, such as a human, the method comprising the step of administering to the mammal an antibody or antibody fragment according to the first aspect of the present invention, or a pharmaceutical composition according to the second aspect of the present invention.

The metabolic disease to be addressed and/or treated in accordance with the third aspect of the present invention may, for example, be a condition selected from the group consisting of metabolic syndrome, insulin resistance, glucose intolerance, hyperglycemia, type I diabetes, type II diabetes, hyperlipidemia, hypertriglyceridemia, hypercholesterolemia, dyslipidemia, and polycystic ovary syndrome (PCOS).

A fourth aspect of the present invention provides a nucleic acid molecule comprising a sequence encoding an antibody or an antibody fragment, or polypeptide chain forming part of the antibody or an antibody fragment, according to the first aspect of the invention. The nucleic acid molecule may, for example, be DNA or RNA. The nucleic acid molecule may comprise additional sequence 5' and/or 3' to the sequence encoding the, or part of, the antibody or an antibody fragment according to the first aspect of the invention. Such 5' and 3' sequences may include transcriptional and/or translational regulatory sequences, such as promoter and/or terminator sequences which are well known in the art and may, for example, be selected in order to be functional in a host cell of choice. Accordingly, the nucleic acid molecule may comprise an expression cassette that, following transformation into a host cell of choice, can be expressed by the transcriptional and/or translational systems of the host cell to result in the production of the encoded antibody or an antibody fragment, or polypeptide chain forming part of the antibody or an antibody fragment, according to the first aspect of the invention.

A fifth aspect of the present invention provides a vector or plasmid comprising one or more nucleic acid sequences according to the fourth aspect of the invention. Where the antibody or antibody fragment comprises more than one polypeptide chain, the vector or plasmid may, for example, comprise a nucleic acid coding sequence encoding each polypeptide chain, such that a host cell transformed with the vector or plasmid can express all polypeptide chains present in the antibody or antibody fragment.

Accordingly, the fifth aspect also provides for the use of a vector or plasmid in the transformation of a host cell. Methods of transforming host cells with vectors or plasmids are well known in the art. To aid the selection of transformed host cells, the vector or plasmid may comprise a selectable marker.

A sixth aspect of the present invention provides a host cell comprising one or more vectors or plasmids according to the fifth aspect of the invention. The sixth aspect also provides for a culture of cells comprising the one or more vectors or plasmids according to the fifth aspect of the invention, such as monoculture in which all or substantially all cells comprise the same one or more vectors or plasmids according to the fifth aspect of the invention. Such monocultures can be obtained, for example, by selecting cells for the presence of one or more selectable markers on the one or more plasmids or vectors and optionally maintaining the selective pressure during the growth of the selected cell in culture.

Where the antibody or antibody fragment according to the first aspect of the present invention comprises more than one polypeptide chain, the host cell may be transformed with a single vector or plasmid that comprises a nucleic acid coding sequence encoding each polypeptide chain, such that a host cell transformed with the vector or plasmid can express all polypeptide chains present in the antibody or antibody fragment.

Alternatively, where the antibody or antibody fragment according to the first aspect of the present invention comprises more than one polypeptide chain, the host cell may be transformed with more than one vector or plasmid that each comprises a nucleic acid coding sequence encoding at least one of the polypeptide chains, such that a host cell transformed with the more than one vectors or plasmids can express all polypeptide chains present in the antibody or antibody fragment.

In a further alternative, where the antibody or antibody fragment according to the first aspect of the present invention comprises more than one polypeptide chain, multiple host cells may each be transformed with a vector or plasmid that each comprises a different nucleic acid coding sequence each encoding one or more different members of the different polypeptide chains that form the antibody or antibody fragment, and each different host cell cultured separately to express each polypeptide chain. The recovered different polypeptide chains can then be combined to produce the antibody or antibody fragment.

Any suitable host cell can be used in the fifth and/or sixth aspects of the invention. For example, the host cell may be a prokaryotic cell, such as an *Escherichia coli* cell. The host cell may be an eukaryotic cell, such as animal cell, a plant cell, and a fungal cell. Suitable animal cells may include mammalian cells, avian cells, and insect cells. Suitable mammalian cells can include CHO cells, and COS cells.

Suitable fungal cells can include yeast cells, such as a *Saccharomyces cerevisiae* cells. Mammalian cells may, or may not, include human cells, and may or may not include embryonic cells.

A seventh aspect of the present invention provides a method for producing an antibody or an antibody fragment antigen-binding sequence according to the first aspect of the present invention comprising culturing one or more transformed host cells as described above, and recovering therefrom an antibody or an antibody fragment according to the first aspect of the present invention.

An eighth aspect of the present invention provides a method of preparing a variant of the antibody or antibody fragments of the first aspect of the present invention, which variant retains the ability to bind to phosphorylcholine and/or a phosphorylcholine conjugate, the method comprising—
  (i) providing a nucleic acid according to the fourth aspect of the present invention encoding a parent antibody or antibody fragment or polypeptide chain forming part thereof;
  (ii) introducing one or more nucleotide mutations (optionally, up to 50, 40, 30, 20, 15, 10, 9, 8, 7, 6, 5, 4, 3, 2, or 1 nucleotide mutations), into the amino acid coding regions of the nucleic acid sequence, optionally within the regions encoding the VH and/or VL domain(s), such that the mutated nucleic acid encodes a variant antibody or antibody fragment having a different amino acid sequence compared to the parent antibody or antibody fragment;
  (iii) expressing the variant antibody or antibody fragment, or polypeptide chain forming part thereof, that is encoded by the mutated nucleic acid sequence; and
  (iv) comparing the ability of the variant antibody or antibody fragment and the parent antibody or antibody fragment to bind to phosphorylcholine and/or a phosphorylcholine conjugate.

In accordance with the eighth aspect of the present invention, nucleotide mutations may be introduced into the amino acid coding regions of the nucleic acid sequence randomly, or in a site-directed manner. Such mutations may result in the coding region encoding an amino acid sequence that contains one or more amino acid additions, one or more amino acid deletions and/or one or more amino acid substitutions compared to the amino acid sequence encoded by nucleic acid prior to mutation.

Such nucleotide mutations may, or may not, result in the coding region encoding an amino acid sequence that contains one or more variations in sequence in the antigen binding region. Such nucleotide mutations may, for example, result in amino acid sequence variation (that is, one or more amino acid additions, one or more amino acid deletions and/or one or more amino acid substitutions) present in, or exclusively in, the amino acid sequence that form one or more of the framework regions. Additionally or alternatively, such nucleotide mutations may, for example, result in amino acid sequence variation (that is, one or more amino acid additions, one or more amino acid deletions and/or one or more amino acid substitutions) present in, or exclusively in, the amino acid sequence that form one or more of the complementarity determining regions. Levels of amino acid variations/modifications tolerated in respect of framework regions, CDRs and/or VH or VL domains as whole are discussed above in respect of the first aspect of the present invention and may be applied, mutatis mutandis, to the level of variation/modification that can be introduced according to the method of the eighth aspect of the present invention.

Additionally or alternatively, such nucleotide mutations may, or may not, result in the coding region encoding an amino acid sequence that contains one or more variations in sequence in one or more parts of the antibody or antibody fragment other than the antigen binding region, such as in one or more of the CH1, CH2, CH3, CL regions or other regions.

Where one or more nucleotide mutations result in one or more amino acid substitutions in the encoded product, then the one or more substitutions may each, independently, be conservative or non-conservative substitutions. By "conservative substitutions" is intended combinations such as Gly, Ala; Val, Ile, Leu; Asp, Glu; Asn, Gln; Ser, Thr; Lys, Arg; and Phe, Tyr.

Nucleotide mutations may, for example, be introduced in order to render the sequence of the encoded antibody or antibody fragments closer to germline sequences, to improve the stability of the antibody or antibody fragment comprising the variant antigen binding region(s), to reduce the immunogenicity of the antibody or antibody fragment comprising the variant antigen binding region(s), and/or to avoid or reduce properties that could be disadvantageous in the manufacturing process.

Such nucleotide mutations may be made using methods that are well known in the art.

In accordance with the eighth aspect of the present invention, the step of assessing the ability of the variant antibody or antibody fragment to bind to phosphorylcholine and/or a phosphorylcholine conjugate may further comprise selecting those variants that have substantially equal or enhanced ability to bind to phosphorylcholine and/or a phosphorylcholine conjugate compared to the parent.

The ability of variants and parents to bind phosphorylcholine and/or a phosphorylcholine conjugate can be assessed by methods such as those discussed above in respect of the first aspect of the present invention.

The method of the eighth aspect of the present invention may optionally further comprising recovering a nucleic acid molecule that comprises the mutated nucleic acid sequence that encodes the variant antibody or antibody fragment, and optionally transforming a host cell with a composition comprising the recovered nucleic acid molecule and further optionally expressing the variant antibody or antibody fragment from the host cell, and yet further optionally recovering the thus-expressed variant antibody or antibody fragment from the host cell, and yet further optionally, formulating the recovered variant antibody or antibody fragment into a pharmaceutically acceptable composition.

The eighth aspect of the present invention also provides a variant antibody or antibody fragment obtained or obtainable by the method of the eighth aspect of the invention, or a pharmaceutically acceptable obtained or obtainable by the method of the eighth aspect of the invention, for use in medicine.

The eighth aspect of the present invention also provides a variant antibody or antibody fragment obtained or obtainable by the method of the eighth aspect of the invention, or a pharmaceutically acceptable obtained or obtainable by the method of the eighth aspect of the invention, for use in—
 (i) the prevention, prophylaxis and/or treatment of mammals, including humans, against atherosclerosis, an atherosclerotic related disease or cardiovascular disease;
 (ii) in the prophylaxis, prevention and/or treatment of Alzheimer's disease; and/or
 (iii) in the immunization or prophylaxis against, or the prevention or treatment of, metabolic disease in mammals, including humans.

In other words, eighth aspect of the present invention also provides for the use of a variant antibody or antibody fragment obtained or obtainable by the method of the eighth aspect of the invention, or the use of a pharmaceutically acceptable obtained or obtainable by the method of the eighth aspect of the invention, in the manufacture of a medicament for—
 (i) the prevention, prophylaxis and/or treatment of mammals, including humans, against atherosclerosis, an atherosclerotic related disease or cardiovascular disease;
 (ii) in the prophylaxis, prevention and/or treatment of Alzheimer's disease; and/or
 (iii) in the immunization or prophylaxis against, or the prevention or treatment of, metabolic disease in mammals, including humans.

Accordingly, also provided by the eighth aspect of the present invention is a method for—
 (i) prevention, prophylaxis and/or treatment of a mammal, including a human, against atherosclerosis, an atherosclerotic related disease, or cardiovascular disease,
 (ii) immunization and prophylaxis, prevention and/or treatment of a subject against Alzheimer's disease; and/or
 (iii) immunization or prophylaxis against, or the treatment of, metabolic diseases in a mammal, such as a human,
 the method comprising the step of administering to the mammal or subject a variant antibody or antibody fragment obtained or obtainable by the method of the eighth aspect of the invention, or the use of a pharmaceutically acceptable obtained or obtainable by the method of the eighth aspect of the invention.

The metabolic disease to be addressed and/or treated in accordance with the eighth aspect of the present invention may, for example, be a condition selected from the group consisting of metabolic syndrome, insulin resistance, glucose intolerance, hyperglycemia, type I diabetes, type II diabetes, hyperlipidemia, hypertriglyceridemia, hypercholesterolemia, dyslipidemia, and polycystic ovary syndrome (PCOS).

Phosphorylcholine

By phosphorylcholine (PC) is meant phosphorylcholine according to the formula.

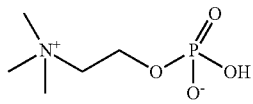

By a phosphorylcholine conjugate is meant a phosphorylcholine moiety linked to a carrier, preferably via a spacer. The phosphorylcholine moiety can be covalently or non-covalently linked to the carrier. Preferably the phosphorylcholine moiety is linked to the carrier via the phosphate group.

The carrier can be, for example, a protein, a carbohydrate, a polymer, latex beads, or colloid metal.

The phosphorylcholine conjugate may for example be a protein-PC conjugate, such as a human serum albumin (HSA)-PC conjugate, a transferrin-PC conjugate, a keyhole limpet hemocyanin (KLH)-PC conjugate or a bovine serum albumin (BSA)-PC conjugate.

Where the PC conjugate comprises PC linked to a carrier via a spacer, then any suitable spacer may be used. Non-limiting examples of spacers include coupling agents (typically, bi-functional compounds), such as a di-carboxylic acids like succinic and glutaric acid, the corresponding di-aldehydes, di-amines such as 1,6 diaminohexane, di-substituted phenols such as p-amino-phenol, p-diazo-phenol, p-phenylenediamine, p-benzoquinone, and the like.

Cardiovascular Disease

The term cardiovascular diseases, is intended to include but is not limited to atherosclerosis, acute coronary syndrome, acute myocardial infarction, myocardial infarction (heart attack), stable and unstable angina pectoris, aneurysms, coronary artery disease (CAD), ischemic heart disease, ischemic myocardium, cardiac and sudden cardiac death, cardiomyopathy, congestive heart failure, heart failure, stenosis, peripheral arterial disease (PAD), intermittent claudication, critical limb ischemia, and stroke.

The treatment or prevention of cardiovascular diseases using antibodies with reactivity to phosphorylcholine and phosphorylcholine conjugates is discussed, for example, in WO 2005/100405 and US 2007-0286868, the contents of both of which are incorporated herein by reference.

Alzheimer's Disease

In accordance with the present invention, antibody or antibody fragments according to the first aspect may be used to treat or prevent Alzheimer's disease in individuals in need or risk thereof.

WO 2010/003602 and U.S. Patent Application No. 61/078,677 describe the treatment or prevention of Alzheimer's disease using antibodies with reactivity to phosphorylcholine and phosphorylcholine conjugates, and the contents of both of which are incorporated herein by reference as further disclosure of ways in which antibody or antibody fragments according to the first aspect may be used to treat or prevent Alzheimer's disease.

Metabolic Diseases

The term metabolic diseases, is intended to include but is not limited to metabolic syndrome X, insulin resistance (IRS), glucose intolerance, hyperglycemia, type I diabetes, type II diabetes, hyperlipidemia, hypertriglyceridemia, hypercholesterolemia, dyslipidemia polycystic ovary syndrome (PCOS) and related diseases.

Further discussion of metabolic diseases to be treated with antibodies with reactivity to phosphorylcholine and phosphorylcholine conjugates are discussed in WO 2012/010291, the contents of which are also incorporated herein by reference for further disclosure of ways in which antibody or antibody fragments according to the first aspect may be used to treat or prevent metabolic diseases.

Amino Acid Sequence Identity

The percent identity between two amino acid sequences is determined as follows. First, an amino acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence followed by multiplying the resulting value by 100. For example, if a sequence is compared to the sequence set forth in SEQ ID NO:A (the length of the sequence set forth in SEQ ID NO:A being 10) and the number of matches is 9, then the sequence has a percent identity of 90% (i.e., 9÷10*100=90) to the sequence set forth in SEQ ID NO:A.

Antibodies

The term "antibody or antibody fragment" as referred to herein in the context of the present invention includes whole antibodies and any antigen binding fragment referred to as "antigen-binding region" or single chains thereof.

An "antibody" may refer to a protein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL.

The VH and VL regions can be further subdivided into regions of hypervariability, termed complementarity determining regions (CDR), interspersed with regions that are more conserved, termed framework regions (FR). Each VH typically comprises three CDRs and four FRs, arranged from amino-terminus to carboxy-terminus in the following order: FR1, CDR1, FR2, CDR2, FR3, CDR3, FR4. Likewise, each VL typically comprises three CDRs and four FRs, arranged from amino-terminus to carboxy-terminus in the following order: FR5, CDR4, FR6, CDR5, FR7, CDR6, FR8. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding region", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding region" of an antibody include—
  (i) a Fab fragment, a monovalent fragment consisting of the VL, VH, CL and CH1 domains;
  (ii) a F(ab')$_2$ fragment, a bivalent fragment comprising two Fab fragments linked by a disulfide bridge at the hinge region;
  (iii) a Fab' fragment, which is essentially an Fab with part of the hinge region;
  (iv) a Fd fragment consisting of the VH and CH1 domains;
  (v) a Fv fragment consisting of the VL and VH domains of a single arm of an antibody,
  (vi) a dAb fragment which consists of a VH domain;
  (vii) an isolated complementarity determining region (CDR); and
  (viii) a nanobody, a heavy chain variable region containing a single variable domain and two constant domains.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Such single chain antibodies are also intended to be encompassed within the term "antigen-binding portion" of an antibody.

Diabodies consists of two polypeptides each comprising a heavy (VH) chain variable domain connected to a light chain variable domain (VL) on the same polypeptide chain ($V_H$-$V_L$) connected by a peptide linker. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds phosphorylcholine is substantially free of antibodies that specifically bind antigens other than phosphorylcholine). Moreover, an isolated antibody may be substantially free of other cellular material and/or chemicals.

The terms "monoclonal antibody" or "monoclonal antibody composition" as used herein refer to a preparation of antibody molecules of single molecular composition.

A monoclonal antibody composition displays a single binding specificity and affinity for a particular epitope.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

Pharmaceutical Compositions

A pharmaceutical composition according to the invention may comprise a binding protein according to the invention in admixture with a pharmaceutically acceptable carrier and/or excipient, which will typically be selected with regard to the intended route of administration and standard pharmaceutical practice. The composition may be in the form of immediate-, delayed- or controlled-release applications. Preferably, the formulation is a unit dosage containing a daily dose or unit, daily sub-dose or an appropriate fraction thereof, of the active ingredient.

The pharmaceutical composition according to the invention may, or may not, be intended for, and, thus formulated in a manner suitable for, parenteral, intravenous, intra-arterial, intraperitoneal, intra-muscular, intra-cerebroventricular, or subcutaneous administration, or they may be administered by infusion techniques. They may be best used in the form of a sterile aqueous solution which may contain other substances, for example, enough salts or glucose to make the solution isotonic with blood or cerebral spinal fluid (CSF). The aqueous solutions may be suitably buffered (preferably to a pH of from 3 to 9), if necessary. The preparation of suitable pharmaceutical formulations under sterile conditions is readily accomplished by standard pharmaceutical techniques well-known to those skilled in the art.

Such formulations may include aqueous and non-aqueous sterile injection solutions which may contain anti-oxidants, buffers, bacteriostats and solutes which render the formulation isotonic with the blood or CSF of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

A therapeutically effective amount of an antibody or an antibody fragment according to the invention for administration to a patient, such as a human patient, on the basis of a daily dosage level may be from 0.01 to 1000 mg of antibody or antibody fragment per adult (for example, from about 0.001 to 20 mg per kg of the patient's body weight, such as 0.01 to 10 mg/kg, for example greater than 0.1 mg/kg and less than 20, 10, 5, 4, 3 or 2 mg/kg, such as about 1 mg/kg), administered in single or divided doses.

The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention

(♦) M99-B05 (lot W21573) (Kd=160±32 nM), (○) M99-B05 (lot W22595) (Kd=148±8 nM). The panel compares these two different preparations of the antibody.

Figure 2:
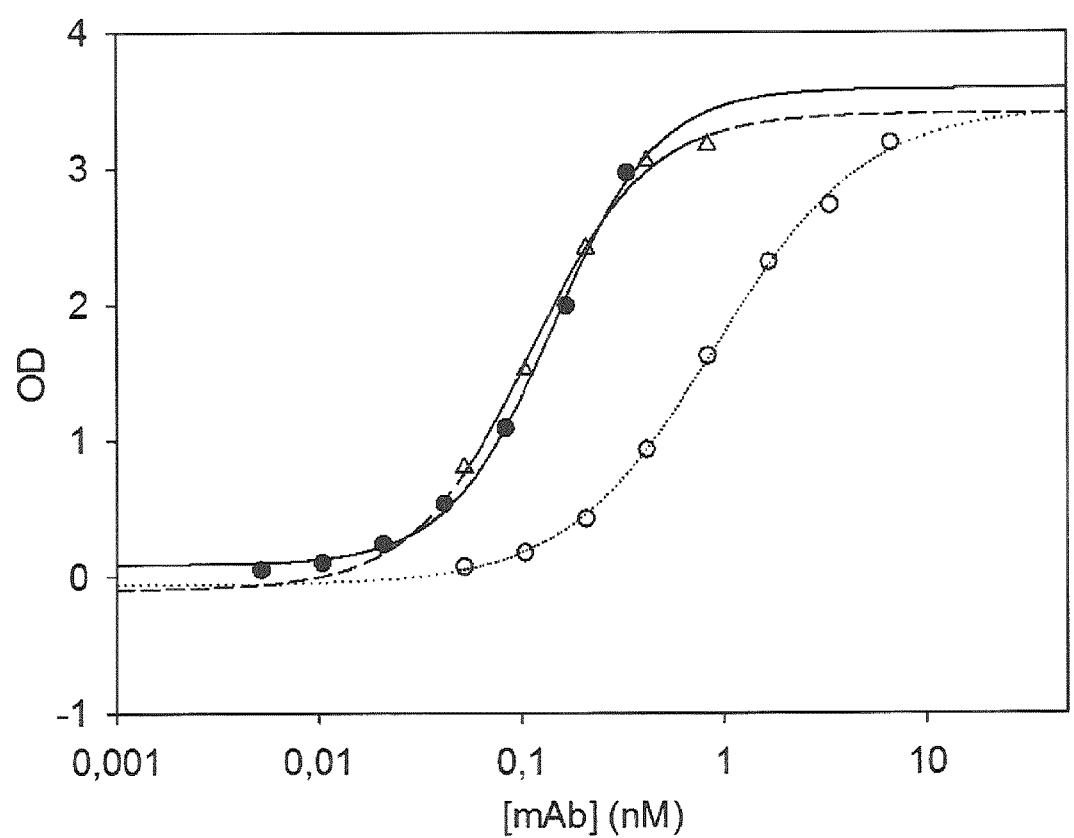

FIG. 2. Purified IgGs Binding to PC-BSA as Measured by ELISA.

(●) M4-G02 ($EC_{50}$=0.14 nM), (○) M73-G03 ($EC_{50}$=0.91 nM), (Δ) M99-B05 ($EC_{50}$=0.11 nM). The data were fit to a 4 parameter logistic equation with a global $B_{max}$ to obtain EC50 value estimates.

Figure 3:
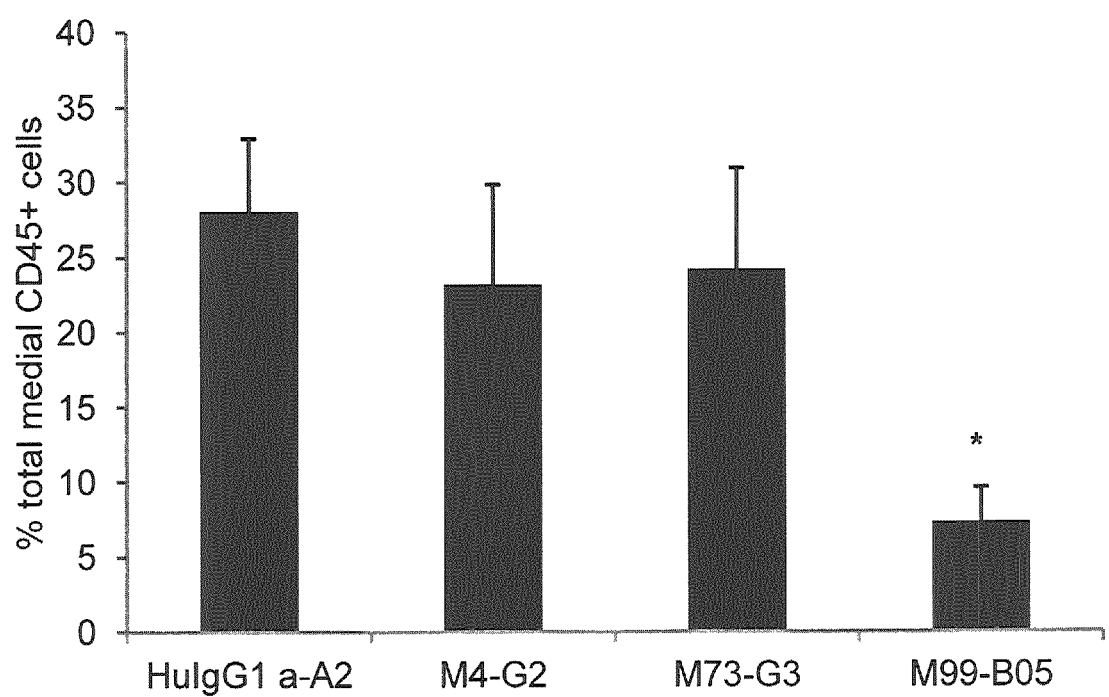

FIG. 3. Inhibition of CD45 Positive Leukocyte Influx into Medial in Femoral Artery Cuffed Mice.

Transgenic male ApoE*3 Leiden mice were fed a high-cholesterol and high-fat diet containing 1% cholesterol and 0.05% cholate to induce hypercholesterolemia. After three weeks of the high fat diet, mice were anesthetized and the femoral artery was dissected from its surroundings and loosely sheathed with a non-constrictive polyethylene cuff (Portex, 0.40 mm inner diameter, 0.80 mm outer diameter and 2.0 mm length). Mice were treated with either 10 mg/kg recombinant anti-PC IgG antibodies dissolved in PBS, 10 mg/kg anti-streptavidin A2 IgG antibodies dissolved in PBS or PBS only through IP injection on day 0. Mice were sacrificed three days after surgery and cuffed femoral arteries were harvested and paraffin-embedded. Serial cross-sections (5 μm) were taken from the entire length of the cuffed femoral artery segment for histochemical analysis. $*p<0.01$, n=15.

Figure 4:
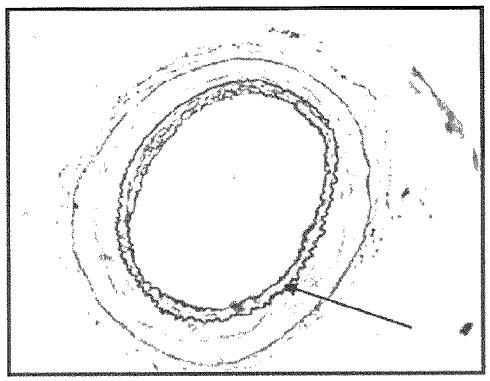
Figure 4:
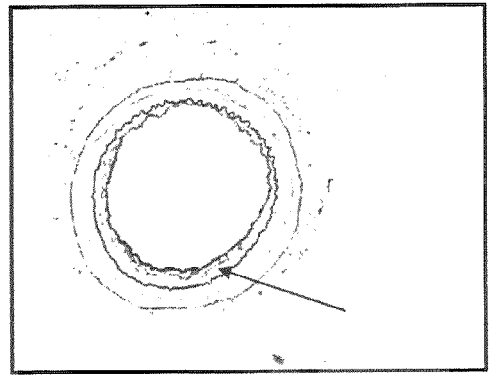
Figure 4:
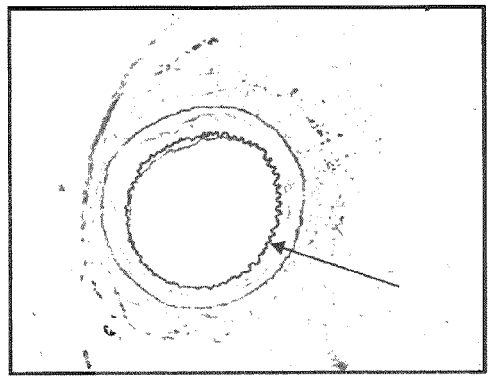
Figure 4:
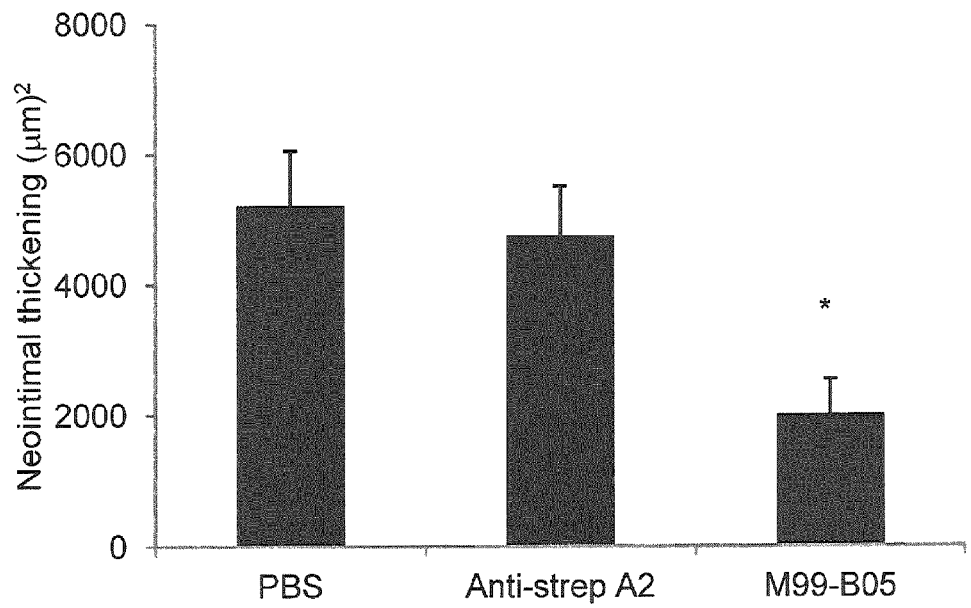

FIG. 4. Inhibition of Intimal Thickening in Femoral Artery Cuffed Mice.

Transgenic male ApoE*3 Leiden mice were fed a high-cholesterol and high-fat diet containing 1% cholesterol and 0.05% cholate to induce hypercholesterolemia. After three weeks of the high fat diet, mice were anesthetized and the femoral artery was dissected from its surroundings and loosely sheathed with a non-constrictive polyethylene cuff (Portex, 0.40 mm inner diameter, 0.80 mm outer diameter and 2.0 mm length). Mice were treated with either 10 mg/kg recombinant anti-PC IgG antibodies dissolved in PBS, 10 mg/kg anti-streptavidin A2 IgG antibodies dissolved in PBS or PBS only through IP injection on day 0, 3, 7, and 10 after surgery. Mice were sacrificed 14 days after surgery and cuffed femoral arteries were harvested and paraffin-embedded. Serial cross-sections (5 μm) were taken from the entire length of the cuffed femoral artery segment for histochemical analysis.

A. Comparison of the intimal area (indicated by the arrow) in the 3 panels indicates that the antibodies M99-B05 reduced the intimal thickening that was observed 14 days after cuff-induced vascular injury.

B. Intimal thickening in $(μm)^2$, n=10, $*p<0.05$

Figure 5:
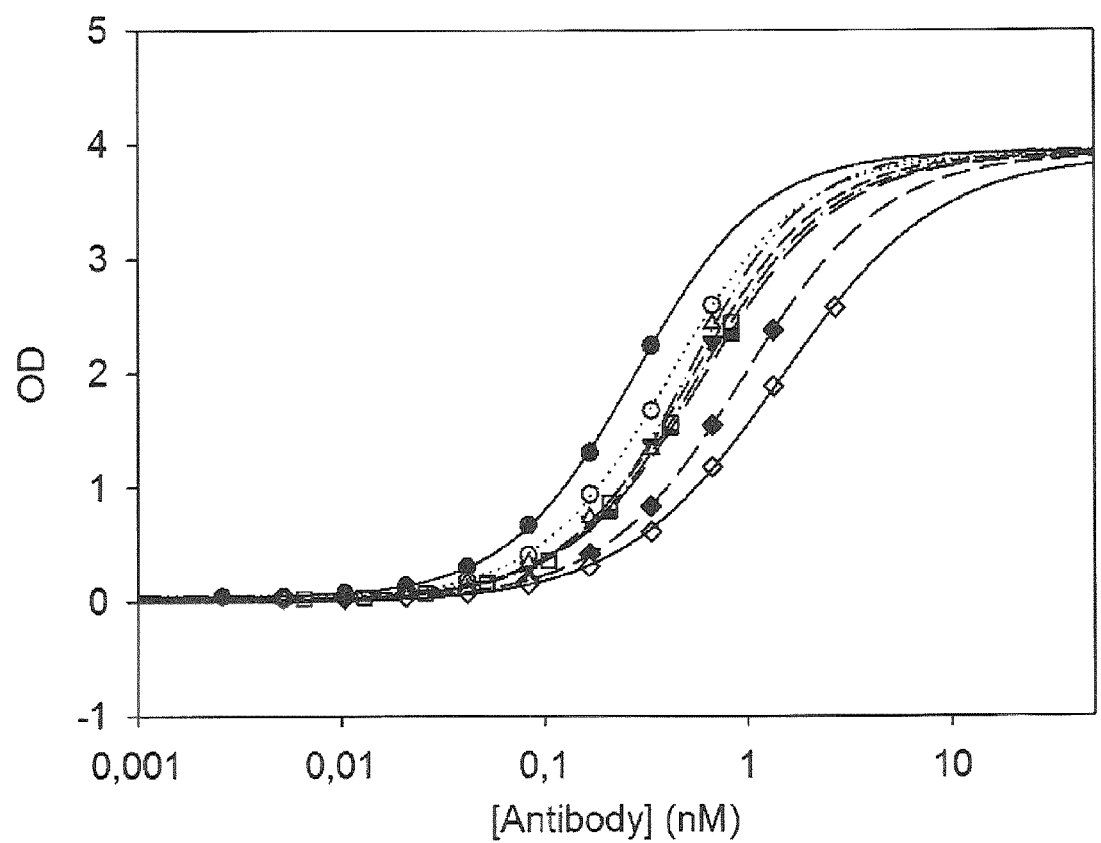

FIG. 5. PC Binding Activity of M99-B05 Mutants Measured Using ELISA (●) M99-B05 ($EC_{50}$=0.28 nM), (○) X19-A01 ($EC_{50}$=0.42 nM), (▼) X19-A03 ($EC_{50}$=0.54 nM), (Δ) X19-A05 ($EC_{50}$=0.52 nM), (■) X19-A07 ($EC_{50}$=0.62 nM), (□) X19-A09 ($EC_{50}$=0.58 nM), (♦) X19-A11 ($EC_{50}$=0.97 nM), (◇) X19-C01($EC_{50}$=1.4 nM).

Figure 6:
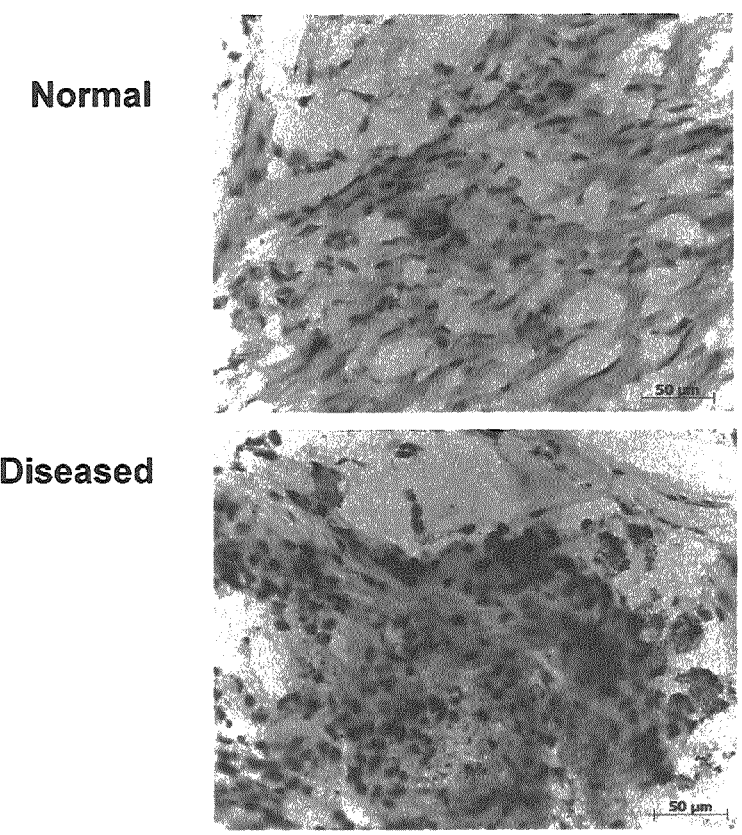

FIG. 6. Immunohistochemistry Staining of Frozen Human Atherosclerotic Lesion Tissue with an Anti-Phosphorylcholine Antibody.

Human atherosclerotic lesion tissue, along with a normal tissue control was obtained commercially from Biochain Human frozen tissues. The tissue was incubated with 0.1 μg/mL biotinylated M99-B05 anti-phosphorylcholine IgG overnight at 4° C. Antibody binding to tissue was visualized following the addition of streptavidin-horse radish peroxidase (HRP) and HRP substrate. The presence of antibody binding is show by the color that is generated from the HRP substrate. No binding was observed with an isotype control (data not shown).

Figure 7:
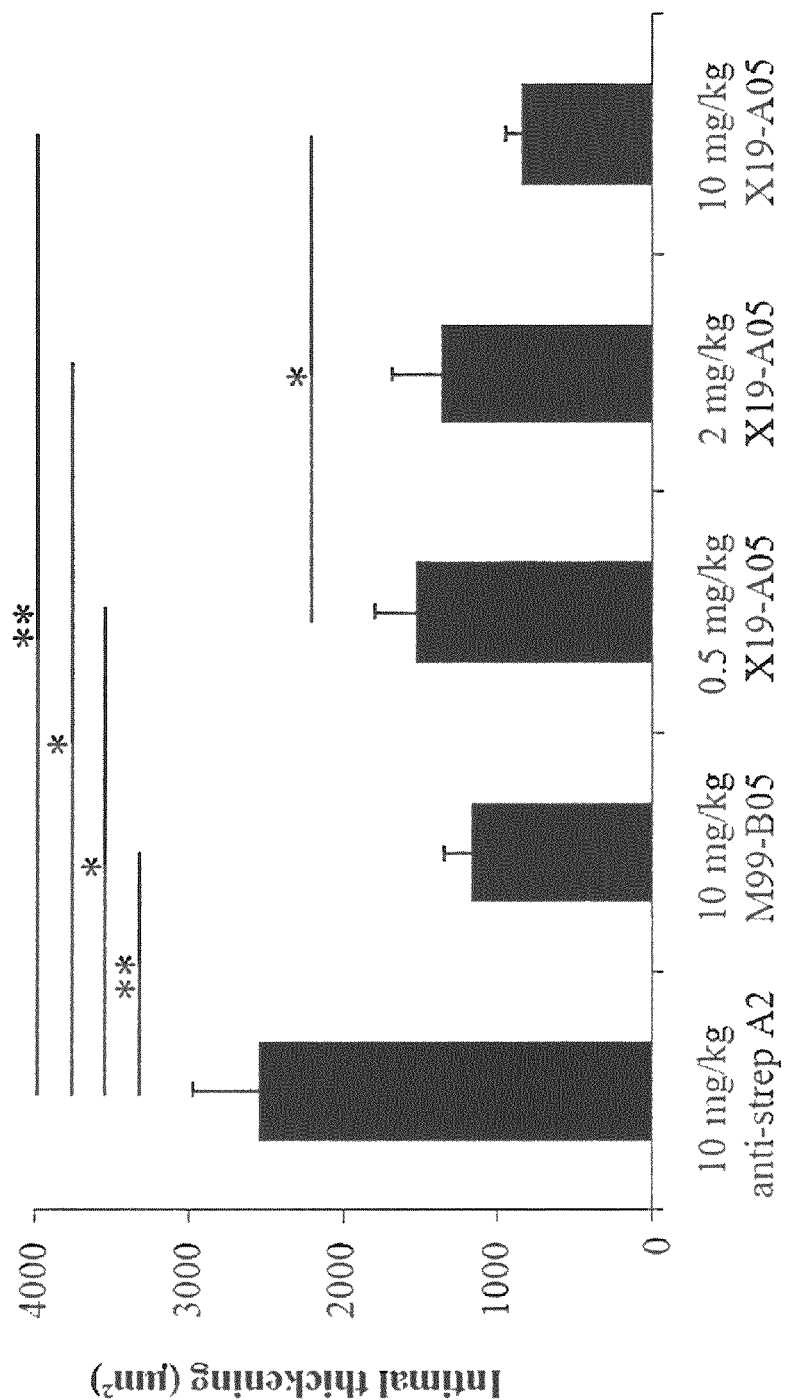

FIG. 7. Inhibition of Intimal Thickening in Femoral Artery Cuffed Mice.

Transgenic male ApoE*3 Leiden mice were fed a high-cholesterol and high-fat diet containing 1% cholesterol and 0.05% cholate to induce hypercholesterolemia. After three weeks of the high fat diet, mice were anesthetized and the femoral artery was dissected from its surroundings and loosely sheathed with a non-constrictive polyethylene cuff (Portex, 0.40 mm inner diameter, 0.80 mm outer diameter and 2.0 mm length). Mice were treated with either the indicated antibody and amount dissolved in PBS by IP injection on day 0, 3, 7, and 10 after surgery. Mice were sacrificed 14 days after surgery and cuffed femoral arteries were harvested and paraffin-embedded. Serial cross-sections (5 μm) were taken from the entire length of the cuffed femoral artery segment for histochemical analysis and the intimal thickening in $(μm)^2$ calculated, n=10, $*p<0.05$.

EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Screening of Phage Display Antibody Library

A phage display selection and screening campaign to identify human antibodies that bind PC and neutralize the pro-inflammatory activity of PC that becomes exposed on oxLDL or apoptotic endothelial cells in cardiovascular disease was performed.

The selection of anti-PC antibodies was directed using PC conjugated to bovine serum albumin (BSA) and alternated between rounds with PC conjugated to ferritin.

The phage display selection output was screened as individual phage for binding to PC-BSA by ELISA and the hits were DNA sequenced to identify the exact number of unique antibodies; all of which were recombinantly converted to IgG. In total, after performing selections on two different phage display libraries 41 fully human IgGs we identified and produced. These antibodies were identified after screening a total of 10,660 different phage clones by ELISA, from which there were 1,511 ELISA positive hits.

An ELISA hit was defined as have a signal on immobilized target (i.e. PC-BSA) that was at least 3-fold greater than the background signal (streptavidin-coated plate).

After sequencing the 1,511 ELISA positives and converting the antibodies from Fab fragments displayed on phage to fully human IgGs, 56 different antibody sequences that bind PC, 26 from the first phagemid library and 30 from the second phage library were recovered.

IgG Reformatting, Expression and Purification

Here we describe the results of recovery of 40 of the 56 antibodies after recombinant reformatting from Fab displayed on phage to full length IgG.

DNA for each IgG was prepared and transfected into human kidney 293T cells to transiently generate IgG after a 10 day media harvest. The IgGs used for in vitro studies were purified using protein A Sepharose (MabSelect) and buffer exchanged into PBS.

IgGs intended for in vivo testing were purified by protein A Sepharose, followed by cation ion exchange (Poros HS) with gradient elution. IgG antibodies intended for in vivo testing were buffer exchanged into Antibody Formulation Buffer (0.1 M citrate-phosphate, 50 mM NaCl, 0.01% Tween-80, 2% Trehalose, pH 6.0). Antibody concentrations were determined on purified samples by absorbance at 280 nm (1 mg/mL=1.4 O.D.).

In Vitro Assays

The 40 IgGs were tested in a battery of in vitro tests to identify the antibodies with the desired properties. Table 1 summarizes binding properties for a selection of fully human IgG Anti-Phosphorylcholine antibodies.

The second column (column A) in Table 1 shows the ELISA signal obtained using only 15.6 ng/mL IgG added to PC-BSA immobilized on a 96 well plate surface. Antibodies with ELISA signals>1 are expected to be higher affinity antibodies.

The third column (column B) in Table 1 shows the signal obtained when the antibodies were injected over aminophenyl phosphorylcholine covalently immobilized on a biosensor chip and binding was detected by surface plasmon resonance using a Biacore 3000 instrument. The higher the Biacore signal, the more binding was observed.

The fourth column (column C) in Table 1 shows the results of test to determine specificity of the antibodies towards phosphorylcholine, by testing for binding to covalently immobilized aminophenol, which is the linker used to covalently couple phosphorylcholine to BSA or the biosensor chip. Several of the antibodies bind the linker molecule as well as, or better than, aminophenyl phosphorylcholine. These antibodies are not likely to be effective therapeutic anti-phosphorylcholine antibodies.

The fifth column (column D) in Table 1 summarizes the results of testing the ability of the antibodies to inhibit the uptake of oxLDL by macrophages, which is an early event in cardiovascular inflammation and leads to the formation of foam cells. The macrophage uptake was monitored by flow cytometry using fluorescently modified oxLDL in the presence or absence of 80 µg/mL tested antibody. In each experiment, 100 µg/mL of affinity purified IgM anti-PC polyclonal antibodies was used as a positive control. The amount of oxLDL taken up in the presence of the tested monoclonal antibodies, as monitored by fluorescence, was divided by the fluorescence observed in the presence of the polyclonal antibody, and then multiplied by 100. Thus, a value below 100 indicate that the antibody in a concentration of 80 µg/mL was more effective in inhibiting oxLDL uptake than the polyclonal anti-PC extracted from human serum in a concentration of 100 µg/mL. A value above 100 similarly indicate that the antibody was less effective than the polyclonal anti-PC.

It was observed that several of the antibodies inhibited the uptake similarly, or better than, the polyclonal anti-PC control. In addition, it was observed that several antibodies stimulated macrophage uptake of oxLDL, a property that excludes these antibodies from lead selection.

The last column (column E) of Table 1 shows ELISA data obtained by adding the IgGs to wells of a 96 well plate that contain either oxLDL or native LDL. The ratio of the ELISA signal observed for binding to oxLDL divided by that observed with LDL is listed in Table 1 for each tested antibody. It is evident that certain antibodies are better binders of oxLDL as compared to LDL.

TABLE 1

Summary of Binding Properties for Fully Human IgG Anti-PC Antibodies

| Sample ID | A | B | C | D | E |
|---|---|---|---|---|---|
| M0004-B02 | 1.24 | 366.4 | 38.6 | 233.3 | 6.7 |
| M0004-C02 | 0.11 | 44.8 | 0.2 | 93 | 1.2 |
| M0004-G02 | 1.23 | 1028.5 | 15.7 | nd | 8.4 |
| M0007-H10 | 0.49 | 415.8 | 2.7 | 105 | 0.6 |
| M0009-A06 | 0.48 | 912.1 | 2.5 | 80.5 | 2.8 |
| M0011-F05 | 1.56 | 4473.6 | 155.6 | 547.5 | 10.3 |
| M0024-B01 | 0.26 | nd | nd | nd | 11.1 |
| M0026-H05 | 0.03 | 1.6 | 17.8 | 73.7 | 1.4 |
| M0027-H05 | 0.03 | −3.3 | 1.4 | 79.3 | 1.1 |
| M0028-H05 | 0.03 | 1.8 | 5 | 86 | 0.6 |
| M0029-H05 | 0.08 | nd | nd | 370 | 0.9 |
| M0030-H05 | 0.02 | 19.1 | 32.8 | nd | nd |
| M0031-H05 | 0.03 | −4.1 | 0.2 | 81 | 1 |
| M0034-G12 | 0.84 | 462.3 | 14.6 | 78 | nd |
| M0035-E11 | 0.14 | 41.5 | 2.1 | 68 | 0.5 |
| M0039-H05 | 2.73 | −6.4 | 2.1 | 80.4 | 0.7 |
| M0042-G07 | nd | −2.9 | 2.3 | 93.7 | 0.8 |
| M0043-D09 | 1.24 | 172.7 | 2.1 | 1310 | 16.8 |
| M0050-H09 | 0.22 | 279.1 | 7 | 71.5 | nd |
| M0073-G03 | 0.18 | 46.3 | 19.9 | 51.1 | 1.2 |
| M0077-A11 | 0.26 | 836.3 | 1.3 | 78.4 | 0.7 |
| M0086-F02 | 0.99 | 1.4 | 12.6 | 315 | nd |
| M0086-H01 | 0.41 | 51.2 | 4.9 | 85 | 1 |
| M0086-H11 | 1 | −1.1 | 0.9 | 74 | nd |
| M0097-B04 | 0.22 | 109.5 | −0.5 | 98 | 1.3 |
| M0097-B05 | 1.01 | 699.6 | −3.2 | 80 | 1.1 |
| M0099-B05 | 1.03 | 5219.3 | 23.3 | 71 | 1.5 |
| M0099-D11 | 0.03 | 170.7 | 8.6 | 560 | 2.1 |
| M0100-A01 | 1.53 | 7532.8 | 3934.7 | nd | 1.1 |
| M0102-E11 | 0.02 | 1.6 | −1.3 | 83 | nd |
| M0108-H03 | nd | 532.7 | 4.5 | nd | 1.1 |
| M0126-A04 | 0.03 | 34.2 | −8 | nd | 2.8 |
| M0126-F10 | nd | 32.9 | −8.3 | nd | nd |
| M0126-H08 | 0.03 | 114.3 | 566.1 | 98 | nd |
| M0127-A09 | 0.03 | 18.2 | −8.7 | 160 | 1.6 |
| M0127-B07 | 0.05 | 16.3 | −7 | 67 | nd |
| M0127-E06 | nd | 21.9 | −4.2 | nd | nd |
| M0127-E07 | nd | 15.4 | −6.2 | nd | 1.8 |
| M0127-F01 | 0.02 | 9.6 | 3.6 | 77 | nd |
| X0009-A01 | 0.23 | 198.1 | 2 | 95 | 1.5 |

Full Column Headings:
A) Binding to PC conjugated to BSA by ELISA at 15.6 ng/ml Ab (OD)
B) Binding to aminophenyl PC by Biacore (RU)
C) Binding to aminophenol linker by Biacore (RU)
D) Percent oxLDL Uptake by Macro-phages in presence of 80 µg/ml Ab (a)
E) Binding to oxLDL versus LDL by ELISA (oxLDL signal/LDL signal) (b)

a) OxLDL Uptake by Macrophages

The uptake of Dil-labelled (1,1'-dioctadecyl-3,3,3",3"-tetramethylindocarbocyanine perchlorate) Cu-oxidized LDL (oxLDL, Intracel Corp, US) was investigated in macrophages that were derived from human THP-1 monocytes (ATCC, US). Differentiation was induced by incubation with 100 nM PMA (Sigma-Aldrich) in RPMI and 10% FCS for 24 h, after which medium was replaced and cells left for another 48 hours. Cells were then incubated with antibodies as indicated at 37° C. for 50-60 min. Thereafter, 20 µg/ml oxLDL was added and incubation continued for 5 hours. At the end of the incubation period, cells were washed two times with ice-cold PBS/0.2% BSA and once with PBS. The cells were harvested in PBS containing 2% PFA. For data acquisition and analysis, FACS Calibur with Cell Quest software was used. For each sample, a minimum of 10.000 cells were analyzed.

b) OxLDL ELISA.

hLDL (Kalen Biomedical #770200-4), oxLDL (Kalen Biomedical #770252-7) (as these data are not shown) were coated at a concentration of 10 µg/ml and a volume of 100 µl/well on an ELISA plate (Immulon 2HB) overnight at 4° C. Plates were blocked with a 1% BSA solution (300 µl/well) for 2 hours at room temperature. After washing, the plate was incubated with the indicated antibodies (100 µl/well; 25-100 nM) for 1 hour at room temperature. AP-conjugated goat anti-human secondary antibody (Thermo-Scientific #31316) at a 1:5000 dilution was added to the washed plate at 100 µl/well and incubated for 1 hour at room temperature. Detection reagent (ThermoScientific #37621) was added (100 µl/well) and the plate was immediately read in kinetic mode at 405 nm with the temperature at 30° C. Results are shown as $OD_{oxLDL}/OD_{LDL}$.

Analysis of Anti-PC IgG Affinity to PC by SPR.

The IgGs were screened for binding to PC using the Biacore surface plasmon resonance (SPR) biosensor. Aminophenyl phosphorylcholine (Biosearch Technologies) was coupled through the free amine group to one flow cell of a CM5 chip to a density of 120 RU. The aminophenol linker was coupled to another flow cell of the same CM5 chip to a density of approximately 120 RU. PC-KLH and PC-BSA were also coupled to separate flow cells of a CM5 chip.

Using these surfaces with PC immobilized in different contexts, the antibodies were injected at 100 nM at 50 µL/min and binding sensorgrams were obtained. The affinity of M99-B05 was investigated by flowing different concentrations of antibody over the surface at 50 µL/min. Towards this immobilized antigen the antibodies display a fast on rate and a fast off rate, which prevented us from obtaining reliable $k_{on}$ and $k_{off}$ estimates from the kinetic sensorgrams.

Figure 1:
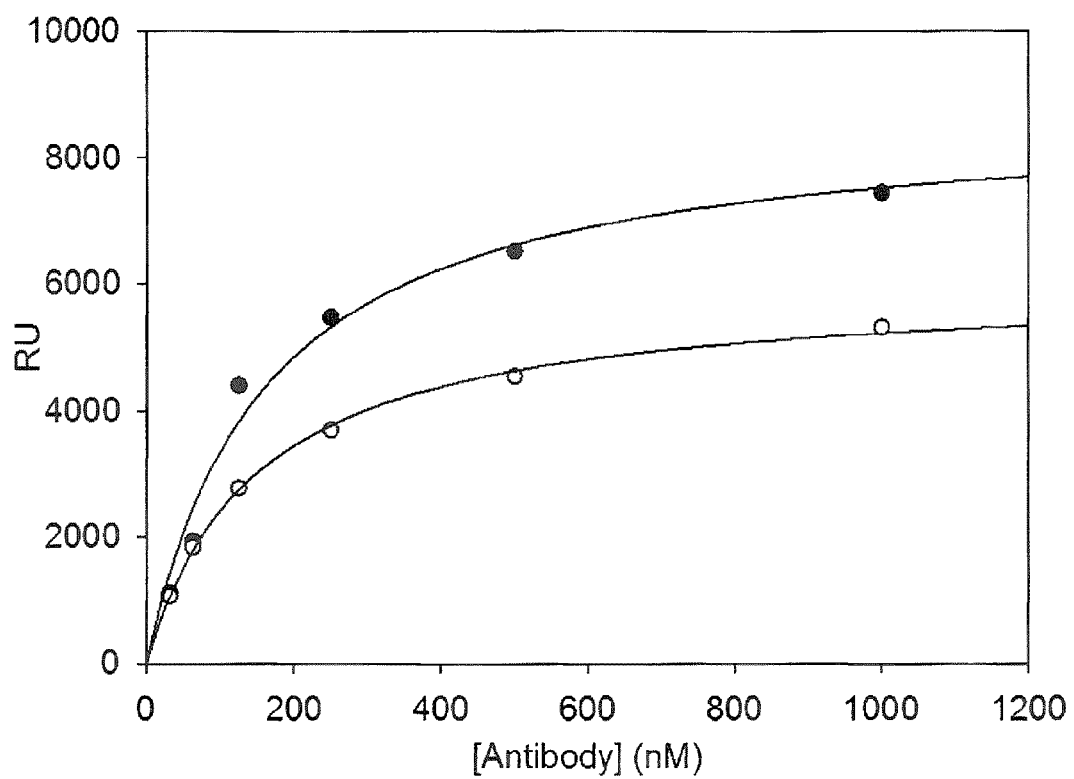
FIG. 1. Estimates of Binding Affinity from an Equilibrium Binding Analysis by Biacore.

The observed signal for each antibody concentration near the end of the injection was plotted versus the antibody concentration and fit the data to a standard hyperbolic equilibrium binding equation (FIG. 1). As seen in FIG. 1, M99-B05 appears to bind aminophenyl PC with an apparent Kd of approximately 150 nM. Both tested preparations having equivalent Kd values but the Rmax (the maximum response) differs. The apparent Kd values observed for each antibody on this surface may or may not represent the affinity observed on more physiological substrates.

ELISA Screening of Purified Anti-PC IgGs

The purified IgGs were also screened for binding to PC using an ELISA with PC-BSA. This data was fitted to provide estimated EC50 values (FIG. 2).

Inhibition of oxLDL Induced MCP-1 Release from Monocytes

Several of the antibodies were tested for their ability to block the release of the chemokine MCP-1 from monocytes in response to stimulation with oxLDL. As shown in Table 2, M99-B05 was very effective in blocking oxLDL-induced MCP-1 release. This antibody potently inhibited MCP-1 release with an $IC_{50}$ in the nM range.

MCP-1 is a potent pro-inflammatory chemokine that promotes the influx of leukocytes at the site of an atherosclerotic lesion (Reape and Groot. 1999. *Chemokines and atherosclerosis. Atherosclerosis* 147, 213-225). Control IgG anti streptavidin A2 as negative control showed no inhibition of oxLDL induced MCP-1 release from monocytes (data not shown).

TABLE 2

Anti-PC inhibition of oxLDL-induced MCP-1 secretion from human monocytes.

| | $IC_{50}$ of M99-B05 |
|---|---|
| Donor 1 | 1.8 ± 0.74 nM |
| Donor 2 | 1.3 ± 0.7 nM |

Moncytes were isolated from human blood and stimulated with 2 µg/mL copper-oxidized oxLDL in the presence or absence of 10 µM to 40 nM anti-PC IgG. MCP-1 levels in the cell media were quantified using a commercially available MCP-1 specific ELISA kit The antibody (M99-B05) was also shown to bind human atherosclerotic lesion tissue (FIG. 6).

In Vivo Assays

Based on a combination of favorable in vitro binding properties and functionality in in vitro assays antibodies M4-G2, M73-G03, and M99-B05 were further tested in an in vivo model of coronary inflammation.

This mouse model measured inflammatory cell influx into the sub-endothelial tissue (i.e. the media) in response to vascular injury induced by placing a restrictive cuff around the exposed femoral artery (FIG. 3). It is evident from FIG. 3 that M99-B05 reduced leukocyte influx into the sub-endothelial layer, the reduction seen being statistically significant. By contrast, and despite their favorable in vitro binding properties and functionality in in vitro assays, neither of M4-G2 or M73-G03 showed any statistically significant reduction compared to the control antibody (the anti-strepavidin A2 IgG termed "HuIgG1a-A2").

The very distinctive effect of M99-B05 in this assay, compared to M4-G2 and M73-G03, could not have been predicted and was a surprise to the inventors. This demonstrates that in vivo efficacy of anti-PC antibodies may not be predictable from positive in vitro data.

Consequently, M99-B05 was tested in a vascular restenosis model in mice, in which injury was again induced by positioning a cuff around the femoral artery but was allowed to progress for 14 days instead of 3 days. The amount of stenosis, observed as a thickening of the vessel neotima in the affected arteries, was then analyzed by histochemistry (FIG. 4). From FIG. 4 it is evident that M99-B05 significantly inhibited vessel wall thickening after cuff-induced vascular injury. This further demonstrates that M99-B05 is highly effective in vivo.

Construction of Germline and Stability Mutants

An amino acid sequence analysis of the variable domains of both the heavy and the light chains of the M99-B05 antibody, identified amino acid substitutions to construct with the intention of reducing potential immunogenicity and avoiding susceptible amino acid modification that may occur during antibody expression and purification.

The following tables show the alignment of the amino acid sequence of the variable domain with its most closely related germline antibody sequence using the Kabat database. Also highlighted in the tables are the amino acid substitutions that were made in the antibody to make it closer to germline, in addition to mutants that removed potential deamidation sites, an HCDR3 disulfide bond, all of which may raise concerns for manufacturability (so called "Stability Mutants").

Mutants of M99-805

The X19-A01 mutant has the same heavy and light amino acid sequences as wild type M99-B05, except that first amino acid of the light chain in M99-B05 (a glutamine) is deleted in X19-A01 to better match the germline sequence.

The sequence of the X19-A03 mutant encodes the fully germlined antibody, relative to the VH3-23, JH3 heavy chain and VK4-B3, JK1 light chain germline sequences, without an inserted phenylalanine (F) in framework 1 of the heavy variable region (HV-FR1), plus amino acid substitutions (stability mutations) to potentially reduce protein amino acid modification during expression and purification. The M99-B05 antibody was found to have a deleted F amino acid at the tail of HV-FR1 relative to the germline sequence. Inserting the F at this position makes the antibody closer to the germline sequence and possibly less likely to be immunogenic. The X19-A03 mutant was constructed to contain all other germline substitutions except the F insertion in the event that this insertion affected PC binding. The stability mutants contain a G to A mutation in the HV-CDR3 that was performed to disrupt a potential deamidation site (NG) and an N to Q substitution in LV-CDR1 to remove another potential deamidation site.

The sequence of the X19-A05 mutant contains all the germline substitutions, including the inserted F in HV-FR1, and the stability mutations. The X19-A05 antibody is the only mutant antibody generated in this example that contains all the germline substitutions and stability mutations.

The X19-A11 mutant has the same sequence as X19-A01 but has two C to S substitutions in the HV-CDR3 to remove the disulfide that is expected to be formed in this region.

The X19-001 is germlined, without the F insertion, and with stability mutants with the C to S substitutions to remove the disulfide. The comparable antibody (pre-disulfide removal) is X19-A03.

TABLE 3

Heavy chain sequence optimization of M99-B05.

| | | |
|---|---|---|
| M99-B05 | EVQLLESGGGLVQPGGSLRLSCAASGFT-S GYWM HWVRQAPGKGLEWVS | |
| X19-A01 | EVQLLESGGGLVQPGGSLRLSCAASGFT-S GYWM HWVRQAPGKGLEWVS | |
| X19-A03 | EVQLLESGGGLVQPGGSLRLSCAASGFT-S GYWM HWVRQAPGKGLEWVS | |
| X19-A05 | EVQLLESGGGLVQPGGSLRLSCAASGFTFS GYWM HWVRQAPGKGLEWVS | |
| X19-A07 | EVQLLESGGGLVQPGGSLRLSCAASGFT-S GYWMH WVRQAPGKGLEWVS | |
| X19-A09 | EVQLLESGGGLVQPGGSLRLSCAASGFTFS GYWM HWVRQAPGKGLEWVS | |
| X19-A11 | EVQLLESGGGLVQPGGSLRLSCAASGFT-S GYWM HWVRQAPGKGLEWVS | |
| X19-C01 | EVQLLESGGGLVQPGGSLRLSCAASGFT-S GYWM HWVRQAPGKGLEWVS | |
| | ****************************** ******************* | |
| M99-B05 | YISPSGGGTHYADSVKG RFTISRDNSKNTLYLQMNSLRAEDTAVYYCAR | |
| X19-A01 | YISPSGGGTHYADSVKG RFTISRDNSKNTLYLQMNSLRAEDTAVYYCAR | |
| X19-A03 | YISPSGGGTHYADSVKG RFTISRDNSKNTLYLQMNSLRAEDTAVYYCAR | |
| X19-A05 | YISPSGGGTHYADSVKG RFTISRDNSKNTLYLQMNSLRAEDTAVYYCAR | |
| X19-A07 | YISPSGGGTHYADSVKG RFTISRDNSKNTLYLQMNSLRAEDTAVYYCAR | |
| X19-A09 | YISPSGGGTHYADSVKG RFTISRDNSKNTLYLQMNSLRAEDTAVYYCAR | |
| X19-A11 | YISPSGGGTHYADSVKG RFTISRDNSKNTLYLQMNSLRAEDTAVYYCAR | |
| X19-C01 | YISPSGGGTHYADSVKG RFTISRDNSKNTLYLQMNSLRAEDTAVYYCAR | |
| | ************************************************* | |
| M99-B05 | VRFRSVCSNGVCRPTAYDAFDI WGQGTAVTVSS | SEQ ID NO: 3 |
| X19-A01 | VRFRSVCSNGVCRPTAYDAFDI WGQGTAVTVSS | SEQ ID NO: 5 |
| X19-A03 | VRFRSVCSNAVCRPTAYDAFDI WGQGTMVTVSS | SEQ ID NO: 7 |
| X19-A05 | VRFRSVCSNAVCRPTAYDAFDI WGQGTMVTVSS | SEQ ID NO: 1 |
| X19-A07 | VRFRSVCSNGVCRPTAYDAFDI WGQGTMVTVSS | SEQ ID NO: 9 |
| X19-A09 | VRFRSVCSNGVCRPTAYDAFDI WGQGTMVTVSS | SEQ ID NO: 11 |
| X19-A11 | VRFRSVSSNGVSRPTAYDAFDI WGQGTAVTVSS | SEQ ID NO: 13 |

TABLE 3-continued

Heavy chain sequence optimization of M99-B05.

```
X19-C01   VRFRSVSSNAVSRPTAYDAFDIWGQGTMVTVSS        SEQ ID NO: 15

******.**.*.************* *****
```

Germlined sequence mutations are shown in bold. Residue mutations that may alleviate possible manufacturing issues are underscored. CDR regions are boxed.

TABLE 4

Light chain sequence optimization of M99-B05

```
M99-B05   QDIQMTQSPDSLAVSLGERATINCKSSQSVFYNSNKKNYLAWYQQKAGQPPKL

X19-A01   -DIQMTQSPDSLAVSLGERATINCKSSQSVFYNSNKKNYLAWYQQKAGQPPKL

X19-A03   -DIVMTQSPDSLAVSLGERATINCKSSQSVFYQSNKKNYLAWYQQKPGQPPKL

X19-A05   -DIVMTQSPDSLAVSLGERATINCKSSQSVFYQSNKKNYLAWYQQKPGQPPKL

X19-A07   -DIVMTQSPDSLAVSLGERATINCKSSQSVFYNSNKKNYLAWYQQKPGQPPKL

X19-A09   -DIVMTQSPDSLAVSLGERATINCKSSQSVFYNSNKKNYLAWYQQKPGQPPKL

X19-A11   -DIQMTQSPDSLAVSLGERATINCKSSQSVFYNSNKKNYLAWYQQKAGQPPKL

X19-C01   -DIVMTQSPDSLAVSLGERATINCKSSQSVFYQSNKKNYLAWYQQKPGQPPKL

** *************************:*************.******

M99-B05   LIHWASTRESGVPDRFSGSGSGTDFTLTISNLQAEDVALYYCQQYFNAPRTF

X19-A01   LIHWASTRESGVPDRFSGSGSGTDFTLTISNLQAEDVALYYCQQYFNAPRTF

X19-A03   LIYWASTRESGVPDRFSGSGSGTDFTLTISSLQAEDVAVYYCQQYFNAPRTF

X19-A05   LIYWASTRESGVPDRFSGSGSGTDFTLTISSLQAEDVAVYYCQQYFNAPRTF

X19-A07   LIYWASTRESGVPDRFSGSGSGTDFTLTISSLQAEDVAVYYCQQYFNAPRTF

X19-A09   LIYWASTRESGVPDRFSGSGSGTDFTLTISSLQAEDVAVYYCQQYFNAPRTF

X19-A11   LIHWASTRESGVPDRFSGSGSGTDFTLTISNLQAEDVALYYCQQYFNAPRTF

X19-C01   LIYWASTRESGVPDRFSGSGSGTDFTLTISSLQAEDVAVYYCQQYFNAPRTF

**:***************************.*******:************

M99-B05   GQGTKVEIK            SEQ ID NO: 4

X19-A01   GQGTKVEIK            SEQ ID NO: 6

X19-A03   GQGTKVEIK            SEQ ID NO: 8

X19-A05   GQGTKVEIK            SEQ ID NO: 2

X19-A07   GQGTKVEIK            SEQ ID NO: 10

X19-A09   GQGTKVEIK            SEQ ID NO: 12

X19-A11   GQGTKVEIK            SEQ ID NO: 14

X19-C01   GQGTKVEIK            SEQ ID NO: 16

*********
```

Germlined sequence mutations are shown in bold. Residue mutations that may alleviate possible manufacturing issues are underscored. CDR regions are boxed.

For the avoidance of doubt, in the event of any inadvertent disparity between the presentation of sequences within this application, the sequences provided for the VH and VL domains and the various CDR sequences in Tables 3 and 4 are the definitive sequences.

PC Binding of the Mutants of M99-B05.

PC binding of the mutants of M99-B05 was assessed by ELISA (FIG. 5). From the ELISA data (FIG. 5) it is evident that many of the mutations in M99-B05 did not significantly affect the binding to PC. However, replacing the cysteine residues in the Hv-CDR3 with serine (X19-A11 and X19-001) did reduce the affinity. These cysteine residues are expected to form a disulfide and are present in the germline antibody sequence encoded by VK4-B3. The differences in the observed binding signals may be attributed to differences in the amount of active antibody in each preparation and/or slight errors in the concentration measurements. The antibody mutant of M99-B05 that contained the maximum number of permissive sequence optimized substitutions was X19-A05. This antibody contained all the stability and germline substitutions but retains the Hv-CDR3 disulfide.

Comparison of the In Vivo Effect of M99-B05 and X19-A05

M99-B05 and X19-A05 were tested in the vascular restenosis model in mice, in which injury was again induced by positioning a cuff around the femoral artery but was allowed to progress for 14 days instead of 3 days. The amount of stenosis, observed as a thickening of the vessel neotima in the affected arteries, was then analyzed by histochemistry and the intimal thickening calculated (FIG. 7). From FIG. 7 it is evident that X19-A05 significantly inhibited vessel wall thickening after cuff-induced vascular injury to a similar extent as compared to M99-B05. The effect of X19-A05 also showed a clear dose-response relation.

The invention claimed is:

1. An antibody or antibody fragment capable of binding to phosphorylcholine and/or a phosphorylcholine conjugate, wherein the antibody or antibody fragment comprises a variable heavy chain (VH) domain and/or a variable light chain (VL) domain, and wherein:

(a) the VH domain comprises an amino acid sequence that comprises a complementarity determining region (CDR)1 having SEQ ID NO: 17, a CDR2 having SEQ ID NO: 18 and a CDR3 having SEQ ID NO: 19; and (b) the VL domain comprises an amino acid sequence that comprises a complementarity determining region (CDR)4 having SEQ ID NO: 23, a CDR5 having SEQ ID NO: 25 and a CDR6 having SEQ ID NO: 26.

2. The antibody or antibody fragment according to claim 1, wherein:

the VH domain comprises an amino acid sequence having at least 80%, 85%, 90%, 95% or 100% sequence identity SEQ ID NO:1; and the VL domain comprises an amino acid sequence having at least 80%, 85%, 90%, 95% or 100% sequence identity SEQ ID NO: 2.

3. The antibody or antibody fragment according to claim 1, wherein the VH domain, the VL domain, or preferably both of the VH and VL domains, comprise an amino acid sequence having 100% sequence identity to the, or one or more (such as all) of SEQ ID NO: 1 and SEQ ID NO: 2, respectively.

4. The antibody or antibody fragment according to claim 1, wherein the VH domain, the VL domain, or both of the VH and VL domains, comprise an amino acid sequence having less than 100%, but at least 80%, 85%, 90%, 95%, sequence identity to the, or one or more (such as all) of SEQ ID NO: 1 and SEQ ID NO: 2, respectively.

5. The antibody or antibody fragment according to claim 1, and wherein the ability of the antibody or antibody fragment to bind to phosphorylcholine and/or a phosphorylcholine conjugate is equivalent to (that is, at least 80%, 85%, 90% or 95%, of), or greater than, the ability of a corresponding antibody or antibody fragment, wherein the VH domain and the VL domain of the corresponding antibody or antibody fragment each comprise an antigen-binding sequence comprising an amino acid sequence having 100% sequence identity to the, or SEQ ID NO: 1 and SEQ ID NO: 2, respectively.

6. The antibody or antibody fragment according to claim 1, wherein the VH domain and the VL domain are present in a linear polypeptide sequence.

7. The antibody or antibody fragment according to claim 1, wherein the VH domain and the VL domain are each present in a separate polypeptide sequence, and preferably wherein the separate polypeptide sequence are directly or indirectly bound together (such as by one or more disulphide bonds between the separate polypeptide sequence).

8. The antibody according to claim 1, wherein the antibody is a monoclonal antibody.

9. The antibody fragment according to claim 1, wherein the antibody fragment is a single chain antibody, Fv, scFv, Fab, F(ab')2, Fab', scFv-Fc fragment, diabody, or any such fragment that has been stabilized such as by PEGylation.

10. The antibody or antibody fragment according to claim 1, which is a human or humanized antibody or antibody fragment, such as a human or humanized monoclonal antibody.

11. The antibody or antibody fragment according to claim 1, which is capable of binding to a phosphorylcholine conjugate.

12. The antibody or antibody fragment according to claim 11, wherein the phosphorylcholine conjugate is a phosphorylcholine moiety linked to a carrier, optionally via a spacer, and preferably the antibody or antibody fragment binds specifically to the phosphorylcholine moiety in the phosphorylcholine conjugate.

13. A pharmaceutical composition comprising or consisting essentially of an antibody or an antibody fragment according to claim 1, and a pharmaceutically acceptable carrier or excipient.

14. A nucleic acid sequence encoding an antibody or an antibody fragment according to claim 1.

15. A vector or plasmid comprising the nucleic acid sequence of claim 14.

16. A host cell comprising the nucleic acid sequence of claim 14.

17. The host cell of claim 16, wherein the cell is a prokaryotic cell, such as an *Escherichia coli* cell, or a eukaryotic cell, such as animal, plant, or fungal cell.

18. The host cell of claim 16, which expresses the nucleic acid sequence to produce an antibody or an antibody fragment.

19. A method of producing an antibody or an antibody fragment comprising culturing a host cell according to claim 18, and recovering therefrom said antibody or antibody fragment.

* * * * *